(12) United States Patent
Hamura et al.

(10) Patent No.: US 12,403,199 B2
(45) Date of Patent: Sep. 2, 2025

(54) ASYMMETRICALLY BRANCHED DEGRADABLE POLYETHYLENE GLYCOL DERIVATIVE

(71) Applicants: NOF CORPORATION, Tokyo (JP); TOKYO INSTITUTE OF TECHNOLOGY, Tokyo (JP)

(72) Inventors: Ken Hamura, Kawasaki (JP); Hiroki Yoshioka, Kawasaki (JP); Kazuki Osakama, Kawasaki (JP); Nobuhiro Nishiyama, Tokyo (JP)

(73) Assignees: NOF CORPORATION, Tokyo (JP); TOKYO INSTITUTE OF TECHNOLOGY, Tokyo (JP)

( * ) Notice: Subject to any disclaimer, the term of this patent is extended or adjusted under 35 U.S.C. 154(b) by 833 days.

(21) Appl. No.: 17/763,516

(22) PCT Filed: Sep. 25, 2020

(86) PCT No.: PCT/JP2020/036199
§ 371 (c)(1),
(2) Date: Mar. 24, 2022

(87) PCT Pub. No.: WO2021/060443
PCT Pub. Date: Apr. 1, 2021

(65) Prior Publication Data
US 2022/0339290 A1    Oct. 27, 2022

(30) Foreign Application Priority Data
Sep. 26, 2019   (JP) ................. 2019-176251

(51) Int. Cl.
*A61K 47/60* (2017.01)
*A61K 47/64* (2017.01)

(52) U.S. Cl.
CPC ............ *A61K 47/641* (2017.08); *A61K 47/60* (2017.08)

(58) Field of Classification Search
CPC ...... A61K 47/641; A61K 47/60; A61K 47/65; A61K 47/64; C07K 5/06078; C08G 65/333; C08G 81/00; C08G 83/003; C08G 65/33324; C08G 2230/00
See application file for complete search history.

(56) References Cited

U.S. PATENT DOCUMENTS

| 2009/0023859 | A1  | 1/2009 | Sakanoue et al. |
| 2010/0010158 | A1* | 1/2010 | McManus ............. A61K 47/60 525/54.1 |
| 2021/0023231 | A1* | 1/2021 | Yoshioka ............. C07K 5/1008 |

FOREIGN PATENT DOCUMENTS

| CN | 104725628 A | 6/2015 |
| CN | 106421806 A | 2/2017 |
| EP | 3778628 A1 | 2/2021 |
| EP | 3950703 A1 | 2/2022 |
| EP | 3950776 A1 | 2/2022 |
| JP | 2009-527581 A | 7/2009 |
| WO | WO-2005/108463 A2 | 11/2005 |
| WO | WO-2006/088248 A1 | 8/2006 |
| WO | WO-2019/189853 A1 | 10/2019 |
| WO | WO-2020/203625 A1 | 10/2020 |
| WO | WO-2020/203626 A1 | 10/2020 |

OTHER PUBLICATIONS

European Medicines Agency, Science Medicines Health, "CHMP Safety Working Party's response to the PDCO regarding the use of PEGylated drug products in the paediatric population", EMA/CHMP/SWP/647258/2012 (Nov. 16, 2012).
Rudmann et al., "High Molecular Weight Polyethylene Glycol Cellular Distribution and PEG-associated Cytoplasmic Vacuolation is Molecular Weight Dependent and Does Not Require Conjugation to Proteins", Toxicologic Pathology, 41:970-983 (2013).
Veronese et al., "PEG-Doxorubicin Conjugates: Influence of Polymer Structure on Drug Release, in Vitro Cytotoxicity, Biodistribution, and Antitumor Activity", Bioconjugate Chem., 16:775-784 (2005).
Vugmeyster et al., "Pharmacokinetic, Biodistribution, and Biophysical Profiles in TNF Nanobodies Conjugated to Linear or Branched Poly(ethylene glycol)", Bioconjugate Chemistry, 23:1452-1462 (2012).
Yang et al., "Synthesis and characterization of enzymatically degradable PEG-based peptide-containing hydrogels", Macromol Biosci., 10(4):445-454 (2010).
International Search Report for PCT/JP2020/036199 dated Dec. 15, 2020.

* cited by examiner

*Primary Examiner* — Kumar R Bhushan
(74) *Attorney, Agent, or Firm* — MARSHALL, GERSTEIN & BORUN LLP

(57) ABSTRACT

A branched degradable polyethylene glycol derivative with a high molecular weight that does not cause vacuolation of cells is provided. A branched degradable polyethylene glycol derivative represented by the following formula (1), containing, in a molecule, an oligopeptide that is degraded in the cells:

$$CH_3O\text{--}(CH_2CH_2O)_{j_1}\text{--}(CH_2)_{k_1}\diagdown_{N\text{--}(CH)_{k_2}\text{--}X}$$
$$CH_3O\text{--}(CH_2CH_2O)_{j_2}\text{--}L_2\text{--}Z\text{--}L_1\text{--}\underset{\underset{O}{\parallel}}{C}\diagup^{\phantom{N}}_{R}$$

(1)

wherein $k_1$ and $k_2$ are each independently 1-12, $j_1$ and $j_2$ are each independently 45-950, R is a hydrogen atom, a substituted or unsubstituted alkyl group having 1-12 carbon atoms, a substituted aryl group, an aralkyl group or a heteroalkyl group, Z is an oligopeptide that is degraded by enzyme in the cells, X is a functional group capable of reacting with a bio-related substance, and $L_1$ and $L_2$ are each independently a single bond or a divalent spacer.

12 Claims, No Drawings

ASYMMETRICALLY BRANCHED DEGRADABLE POLYETHYLENE GLYCOL DERIVATIVE

CROSS REFERENCE TO RELATED APPLICATIONS

This application is a U.S. National Stage of International Application No. PCT/JP2020/036199, filed Sep. 25, 2020, which claims the benefit of Japanese Patent Application No. 2019-176251, filed Sep. 26, 2019, the entire contents of each of which are fully incorporated herein by reference.

TECHNICAL FIELD

The present invention relates to a branched degradable polyethylene glycol derivative that is degraded in the cells and used for modifying bio-related substances.

BACKGROUND ART

Pharmaceutical products that use bio-related substances such as hormone, cytokine, antibody, and enzyme are generally rapidly discharged from the body after administration to the body due to glomerular filtration in the kidney and uptake by macrophages in the liver and spleen. Therefore, the half-life in blood is short, and it is often difficult to obtain a sufficient pharmacological effect. To solve this problem, attempts have been made to chemically modify bio-related substances with sugar chain, hydrophilic polymers such as polyethylene glycol, albumin, and the like. As a result, it becomes possible to prolong the blood half-life of bio-related substances by increasing the molecular weight, forming a hydration layer, and the like. In addition, it is also well known that modification with polyethylene glycol provides effects such as reduction of toxicity and antigenicity of bio-related substances, and improvement of solubility of hardly water-soluble drugs.

The bio-related substances modified with polyethylene glycol are covered with a hydration layer formed by an ether bond of polyethylene glycol and a hydrogen bond with water molecule, has an increased molecular size, and thus can avoid glomerular filtration in the kidney. Furthermore, it is known that the interaction with opsonin and the cell surface that constitutes each tissue decreases, and the migration to each tissue decreases. Polyethylene glycol is a superior material that extends the blood half-life of bio-related substances, and it has been found as regards the property thereof that a higher effect is obtained when the molecular weight is higher. Many studies have been made on bio-related substances modified with high-molecular-weight polyethylene glycol with a molecular weight of not less than 40,000, and the results show that the half-life in blood thereof can be significantly extended.

Polyethylene glycol is regarded as the optimum standard among the modifying agents used for improving the property of bio-related substances. At present, a plurality of polyethylene glycol-modified formulations is placed on the market and used in medical sites. On the other hand the European Medicines Agency (EMA) reported in 2012 that administration of a bio-related substance modified with high-molecular-weight polyethylene glycol with a molecular weight of 40,000 or more to an animal for a long time at a certain dose or above led to a phenomenon of the generation of vacuoles in the cells of a part of the tissues (non-patent literature 1). In consideration of the facts that there is no report at present that the vacuole formation itself has an adverse effect on the human body, and the dose used in the above EMA report is extremely high compared to the dose generally applied in medical sites, the safety of therapeutic preparations modified with polyethylene glycol having a molecular weight of 40,000 or more which are currently manufactured and sold does not pose any problem. However, in the treatment of very special diseases (e.g., dwarfism), it may be assumed that a treatment protocol in which a polyethylene glycol-modified preparation is administered to a patient at a high dose for a long period of time will be adopted. Therefore, it is expected that a potential demand exists for the development of a polyethylene glycol-modified preparation that does not cause vacuole formation in cells and can be applied even in such a special situation.

In non-patent literature 2, a large excess of polyethylene glycol alone was administered to animals for a long term compared to the dose of general polyethylene glycol-modified preparations. As a result, vacuole was not seen at a molecular weight of 20,000, and the generation of vacuole was confirmed at a molecular weight of 40,000. One of the means to suppress vacuoles is to reduce the molecular weight of polyethylene glycol. However, reducing the molecular weight causes a problem that the half-life in blood of bio-related substances cannot be improved sufficiently.

There are reports relating to the technique for degrading high-molecular-weight polyethylene glycol into low-molecular-weight polyethylene glycol in the body and promoting excretion from the kidney. Patent literature 1 describes a polyethylene glycol derivative having a sulfide bond or peptide binding site that is cleaved in vivo. It is described that the polyethylene glycol derivative is degraded in vivo to a molecular weight suitable for excretion from the kidney. However, no specific data relating to the degradation is shown, nor is there any data on enhanced excretion from the kidney. Furthermore, there is no description about the vacuoles in cells.

Patent literature 2 describes a polyethylene glycol derivative having an acetal site that can be hydrolyzed under low pH environment in the body. It is described that the polyethylene glycol derivative is degraded in vivo to a molecular weight suitable for excretion from the kidney. However, no specific data on enhanced excretion from the kidney is shown. Furthermore, there is no description about the vacuoles in cells. In addition, the hydrolyzable acetal moiety is known to gradually degrade also in blood, and it is expected that the half-life in blood of modified bio-related substances cannot be improved sufficiently.

On the other hand there are reports on polyethylene glycol derivatives containing degradable oligopeptides introduced thereinto for effective release of drugs, hydrogels that degrade in the body, and the like.

Non-patent literature 3 describes a polyethylene glycol derivative having an oligopeptide site that is degraded by enzymes. Here, the oligopeptide was introduced as a linker between an anticancer agent and polyethylene glycol, and it has been reported that the oligopeptide is degraded by the enzyme specifically expressed around the tumor, and the anticancer agent is efficiently released. The purpose is release of an anticancer agent, and the degradability is not imparted to polyethylene glycol for the purpose of suppressing cell vacuoles.

Non-patent literature 4 describes hydrogels using cross-linking molecules having an oligopeptide site that is degraded by enzymes and a multi-branched polyethylene glycol derivative. Here, the oligopeptide is used as a cross-linking molecule that connects the multi-branched polyethylene glycol derivative, and can further impart degradability by enzymes to the hydrogel. It aims to prepare a degradable hydrogel, where the degradability is not imparted to polyethylene glycol for the purpose of suppressing cell vacuoles.

Patent literature 3 describes a branched polyethylene glycol derivative with oligopeptide as the skeleton. Here, oligopeptide is used as the basic skeleton of polyethylene glycol derivatives and does not impart degradability by enzymes. It is characterized by containing amino acids having an amino group or a carboxyl group in the side chain, such as lysine and aspartic acid, in the oligopeptide, and aims to synthesize a branched polyethylene glycol derivative by utilizing them in the reaction. Patent literature 3 is not directed to a polyethylene glycol derivative for the purpose of suppressing cell vacuoles.

Polyethylene glycol derivatives used for modifying bio-related substances generally include a linear type and a branched type. Non Patent Literature 5 describes that the branched type, rather than the linear type, significantly prolongs the half-life in blood of bio-related substances. In recent years, most of the polyethylene glycol-modified preparations on the market adopt the branched type. However, there have been no reports on a branched polyethylene glycol derivative that suppresses cell vacuoles.

As described above, a branched high-molecular-weight polyethylene glycol derivative that is stable in blood, improves half-life in blood of the modified bio-related substance, is specifically degraded in cell when taken up by cells, and can suppress generation of vacuoles in cells is demanded.

CITATION LIST

Patent Literature

[PTL 1]
Japanese Translation of PCT Application Publication No. 2009-527581
[PTL 2]
WO2005/108463
[PTL 3]
WO2006/088248

Non Patent Literature

[NPL 1]
EMA/CHMP/SWP/647258/2012
[NPL 2]
Daniel G. Rudmann, et al., Toxicol. Pathol., 41, 970-983 (2013)
[NPL 3]
Francesco M Veronese, et al., Bioconjugate Chem., 16, 775-784(2005)
[NPL 4]
Jiyuan Yang, et al., Marcomol. Biosci., 10(4), 445-454 (2010)
[NPL 5]
Yulia Vugmeysterang, et al., Bioconjugate Chem., 23, 1452-1462 (2012)

SUMMARY OF INVENTION

Technical Problem

The problem of the present invention is to provide a high-molecular-weight branched polyethylene glycol derivative that does not cause vacuolation of cells. More specifically, it is to provide a branched degradable polyethylene glycol derivative that can be effectively used for modifying bio-related substances, is stable in the blood of living organisms, and is degraded in cells, by an industrially producible method.

Solution to Problem

The present inventors have conducted intensive studies in an attempt to solve the aforementioned problems and invented a branched degradable polyethylene glycol derivative having an oligopeptide that degrades in cells.

Therefore, the present invention provides a branched degradable polyethylene glycol derivative represented by the following formula (1).

[1] A branched degradable polyethylene glycol derivative represented by the following formula (1), comprising, in a molecule, an oligopeptide that is degraded in the cells:

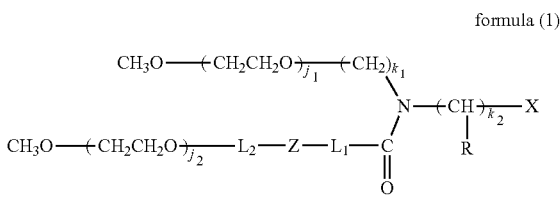

formula (1)

wherein $k_1$ and $k_2$ are each independently 1-12, $j_1$ and $j_2$ are each independently 45-950, R is a hydrogen atom, a substituted or unsubstituted alkyl group having 1-12 carbon atoms, a substituted aryl group, an aralkyl group or a heteroalkyl group, Z is an oligopeptide that is degraded by enzyme in the cells, X is a functional group capable of reacting with a bio-related substance, and $L_1$ and $L_2$ are each independently a single bond or a divalent spacer.

[2] The branched degradable polyethylene glycol derivative of [1], wherein the degradable oligopeptide for Z is an oligopeptide having glycine as a C-terminal amino acid.

[3] The branched degradable polyethylene glycol derivative of any one of [1] and [2], wherein the degradable oligopeptide for Z is an oligopeptide having at least one hydrophobic neutral amino acid having a hydropathy index of not less than 2.5.

[4] The branched degradable polyethylene glycol derivative of any one of [1] to [3], wherein a total molecular weight is not less than 20,000.

[5] The branched degradable polyethylene glycol derivative of any one of [1] to [4], wherein $L_1$ and $L_2$ are each independently a single bond, a urethane bond, an amide bond, an ether bond, a thioether bond, a secondary amino group, a urea bond, or an alkylene group optionally containing such bond and/or group.

[6] The branched degradable polyethylene glycol derivative of any one of [1] to [5], wherein X is selected from the group consisting of an active ester group, an active carbonate group, an aldehyde group, an isocyanate group, an isothiocyanate group, an epoxy group, a maleimide group, a vinylsulfonyl group, an acrylic group, a sulfonyloxy group, a carboxyl group, a thiol group, a dithiopyridyl group, an α-haloacetyl group, an alkynyl group, an allyl group, a vinyl group, an amino group, an oxyamino group, a hydrazide group, and an azide group.

The present invention also provides a branched degradable polyethylene glycol derivative represented by the following formula (2) as other embodiment.

[6] A branched degradable polyethylene glycol derivative represented by the following formula (2):

formula (2)

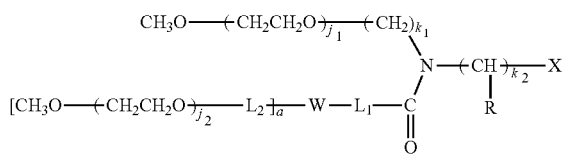

wherein $k_1$ and $k_2$ are each independently 1-12, $j_1$ and $j_2$ are each independently 45-950, R is a hydrogen atom, a substituted or unsubstituted alkyl group having 1-4 carbon atoms, a substituted aryl group, an aralkyl group or a heteroalkyl group, W is oligopeptide of 5-47 residues having a symmetrical structure centered on glutamic acid or lysine, a is 2-8, X is a functional group capable of reacting with a bio-related substance, and $L_1$ and $L_2$ are each independently a single bond or a divalent spacer.

[7] The branched degradable polyethylene glycol derivative of [6], wherein the oligopeptide having a symmetrical structure centered on glutamic acid or lysine for W is an oligopeptide having a structure of the following w1 or w2:

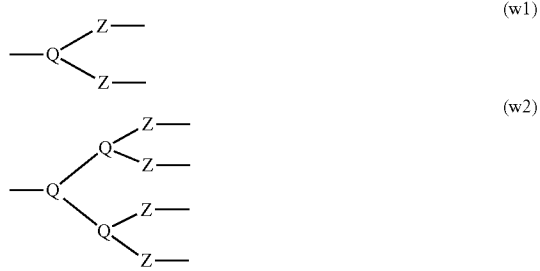

wherein Q is a residue of glutamic acid or lysine, and Z is a degradable oligopeptide of 2-5 residues consisting of neutral amino acids excluding cysteine.

[8] The branched degradable polyethylene glycol derivative of [7], wherein the degradable oligopeptide for Z is an oligopeptide having glycine as a C-terminal amino acid.

[9] The branched degradable polyethylene glycol derivative of [7] or [8], wherein the degradable oligopeptide for Z is an oligopeptide having at least one hydrophobic neutral amino acid having a hydropathy index of not less than 2.5.

[10] The branched degradable polyethylene glycol derivative of any one of [6] to [9], wherein the total molecular weight is not less than 20,000.

[11] The branched degradable polyethylene glycol derivative of any one of [6] to [10], wherein $L_1$ and $L_2$ are each independently a single bond, a urethane bond, an amide bond, an ether bond, a thioether bond, a secondary amino group, a urea bond, or an alkylene group optionally containing such bond and/or group.

[12] The branched degradable polyethylene glycol derivative of any one of [6] to [11], wherein X is selected from the group consisting of an active ester group, an active carbonate group, an aldehyde group, an isocyanate group, an isothiocyanate group, an epoxy group, a maleimide group, a substituted maleimide group, a vinylsulfonyl group, an acrylic group, a substituted sulfonate group, a sulfonyloxy group, a carboxy group, a mercapto group, a pyridyldithio group, an α-haloacetyl group, an alkylcarbonyl group, an iodoacetamide group, an alkenyl group, an alkynyl group, a substituted alkynyl group, an amino group, an oxyamino group, a hydrazide group and an azide group.

Advantageous Effects of Invention

The branched degradable polyethylene glycol derivative of the present invention has, in its structure, an oligopeptide which is stable in blood in the body and degraded by intracellular enzymes. Therefore, the branched degradable polyethylene glycol derivative is stable in blood and can impart a half-life in blood that is equivalent to that of a conventional polyethylene glycol derivative without degradability to a bio-related substance. Furthermore, when the branched degradable polyethylene glycol derivative is incorporated into cells, the oligopeptide site of the degradable polyethylene glycol derivative is rapidly degraded, thus suppressing the generation of vacuoles in cells which has been a problem to date. In addition, impurities developed in the production step can be reduced by limiting the oligopeptide introduced into polyethylene glycol to an oligopeptide having glycine as a C-terminal amino acid, whereby the branched degradable polyethylene glycol derivative can be produced industrially.

DESCRIPTION OF EMBODIMENTS

The present invention is explained in detail in the following.

The branched degradable polyethylene glycol derivative of the present invention is represented by the following formula (1).

formula (1)

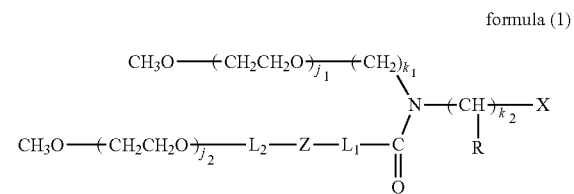

In the formula (1), $k_1$ and $k_2$ are each independently 1-12, $j_1$ and $j_2$ are each independently 45-950, R is a hydrogen atom, a substituted or unsubstituted alkyl group having 1-12 carbon atoms, a substituted aryl group, an aralkyl group or a heteroalkyl group, Z is an oligopeptide that is degraded by enzyme in the cells, X is a functional group capable of reacting with a bio-related substance, and $L_1$ and $L_2$ are each independently a single bond or a divalent spacer.

The total molecular weight of the polyethylene glycol derivative of the formula (1) of the present invention is generally 4,000-160,000, preferably 10,000-120,000, further preferably 20,000-80,000. In one preferred embodiment of the present invention, the total molecular weight of the polyethylene glycol derivative of the formula (1) of the present invention is not less than 20,000. The molecular weight here is a number average molecular weight (Mn).

In the formula (1), $k_1$ and $k_2$ are generally each independently 1-12, preferably each independently 1-6, further preferably each independently 1-2.

In the formula (1), $j_1$ and $j_2$ are each a repeating unit number of polyethylene glycol. Generally, they are each independently 45-950, preferably each independently 110-690, further preferably each independently 220-480.

In the formula (1), R is a hydrogen atom, a substituted or unsubstituted alkyl group having 1-12 carbon atoms, a substituted aryl group, an aralkyl group or a heteroalkyl group. The "heteroalkyl group" is an alkyl group having 1-5 hetero atoms selected from nitrogen atom, oxygen atom and sulfur atom. R is preferably a hydrogen atom or an alkyl group having 1-3 carbon atoms, more preferably a hydrogen atom, a methyl group or an ethyl group, further preferably a hydrogen atom.

In the formula (1), $L_1$ and $L_2$ are each independently a single bond or a divalent spacer, and these spacers are not particularly limited as long as they are groups capable of forming a covalent bond. They are each preferably a phenylene group, an amide bond, an ether bond, a thioether bond, a urethane bond, a secondary amino group, a carbonyl group, a urea bond, or an alkylene group optionally containing such bond and/or group, more preferably an alkylene group, an amide bond, an ether bond, a urethane bond, a secondary amino group, or a group formed by binding a carbonyl group and an alkylene group. Particularly preferred embodiments are shown in the following Group (I). Two to five spacers of Group (I) may be used in combination. An ester bond and a carbonate bond are not suitable as the divalent spacers since they are gradually degraded in the blood of living organisms.

Group (I):

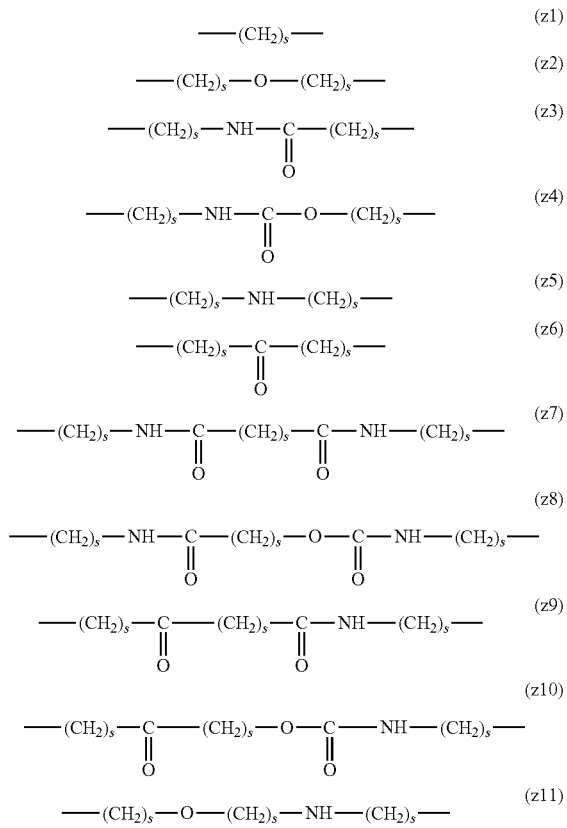

In (z1)-(z11), s is an integer of 0-10, preferably an integer of 0-6, further preferably an integer of 0-3. In (z2)-(z11), each s may be the same or different.

In the formula (1), $L^1$ is preferably a single bond or a combination of (z2), (z3), (z4), (z6), (z7), (z8), (z9), (z10) or (z2), and (z6), more preferably a single bond or a combination of (z3), (z6), (z9), (z10) or (z2), and (z6), in Group (I).

In the formula (1), $L_2$ is preferably (z1), (z2), (z3), (z4), (z5), (z6), (z7), (z8) or (z11), more preferably (z3), (z5) or (z11), in Group (I).

In the formula (1), Z is not particularly limited as long as it is an oligopeptide stable in the blood of living organisms and degraded by enzyme in cells. An oligopeptide of 2-8 residues consisting of neutral amino acids excluding cysteine is preferred, an oligopeptide of 2-6 residues consisting of neutral amino acids excluding cysteine is more preferred, and an oligopeptide of 2-4 residues consisting of neutral amino acids excluding cysteine is further preferred.

In the formula (1), Z is preferably an oligopeptide composed of neutral amino acids not including an amino acid having an amino group or a carboxyl group in the side chain, specifically, lysine, aspartic acid, or glutamic acid. The amino acid used here is α-amino acid and is basically in the L form.

Cysteine, which is a neutral amino acid, has a thiol group and forms a disulfide bond with other thiol groups. Thus, in the formula (1), Z is desirably an oligopeptide composed of neutral amino acids not including cysteine.

In the formula (1), moreover, Z is preferably an oligopeptide having glycine as the C-terminal amino acid. When a C-terminal carboxyl group is reacted with a polyethylene glycol derivative, it is basically necessary to activate the C-terminal carboxyl group with a condensing agent and the like. It is known that epimerization tends to occur in amino acids other than glycine and stereoisomer is by-produced in this activation step. By using an achiral glycine as the C-terminal amino acid of the oligopeptide, a highly pure target product free from by-production of stereoisomer can be obtained.

In the formula (1), moreover, Z is preferably an oligopeptide having at least one hydrophobic neutral amino acid having a hydropathy index of not less than 2.5, specifically, phenylalanine, leucine, valine, or isoleucine, more preferably an oligopeptide having phenylalanine. The hydropathic index (hydropathy index) created by Kyte and Doolittle that quantitatively indicates the hydrophobicity of amino acid shows that the larger the value, the more hydrophobic the amino acid (Kyte J & Doolittle R F, 1982, J Mol Biol, 157:105-132.).

In the formula (1), Z is not particularly limited as long as it is an oligopeptide with 2-8 residues composed of neutral amino acids excluding cysteine, is stable in the blood of living organisms, and has property of degradation by an enzyme in cells. Specific examples include glycine-phenylalanine-leucine-glycine, glycine-glycine-phenylalanine-glycine, glycine-phenylalanine-glycine, glycine-leucine-glycine, valine-citrulline-glycine, valine-alanine-glycine, glycine-glycine-glycine, phenylalanine-glycine and the like, preferably glycine-phenylalanine-leucine-glycine, glycine-glycine-phenylalanine-glycine, glycine-phenylalanine-glycine, glycine-glycine-glycine, valine-citrulline-glycine, valine-alanine-glycine, or phenylalanine-glycine, more preferably glycine-phenylalanine-leucine-glycine, glycine-phenylalanine-glycine, valine-citrulline-glycine, or valine-alanine-glycine, further more preferably glycine-phenylalanine-leucine-glycine, or valine-citrulline-glycine.

In the formula (1), $X^1$ is not particularly limited as long as it is a functional group that reacts with a functional group present in bio-related substances such as a bioactive protein, peptide, antibody, or nucleic acid to be chemically modified to form a covalent bond. For example, the functional groups described in "Harris, J. M. Poly (Ethylene Glycol) Chemistry; Plenum Press: New York, 1992", "Hermanson, G. T. Bioconjugate Techniques, 2nd ed.; Academic Press: San Diego, CA, 2008" and "PEGylated Protein Drugs: Basic Science and Clinical Applications; Veronese, F. M., Ed.; Birkhauser: Basel, Switzerland 2009" and the like can be mentioned.

In the formula (1), the "functional group capable of reacting with a bio-related substance" for X is not particularly limited as long as it is a functional group that can be chemically bonded to a functional group of a bio-related substance such as amino group, mercapto group, aldehyde group, carboxyl group, unsaturated bond or azide group and the like.

Specifically, active ester group, active carbonate group, aldehyde group, isocyanate group, isothiocyanate group, epoxy group, carboxyl group, mercapto group, maleimide group, substituted maleimide group, hydrazide group, dithiopyridyl group, substituted sulfonate group, vinylsulfonyl group, amino group, oxyamino group ($H_2N-O-$ group), iodoacetamide group, alkylcarbonyl group, alkenyl group (e.g., allyl group, vinyl group), alkynyl group, substituted alkynyl group (e.g., alkynyl group substituted by hydrocarbon group with carbon number of 1-5 to be described later), azide group, acrylic group, sulfonyloxy group (e.g., alkylsulfonyloxy group), α-haloacetyl group and the like can be mentioned. It is preferably active ester group, active carbonate group, aldehyde group, isocyanate group, isothiocyanate group, epoxy group, maleimide group, substituted maleimide group, vinylsulfonyl group, acrylic group, sulfonyloxy group (e.g., alkyl-sulfonyloxy group with carbon number of 1-5), substituted sulfonate group, carboxyl group, mercapto group, pyridyldithio group, α-haloacetyl group, alkynyl group, substituted alkynyl group (e.g., alkynyl group with carbon number of 2-5 and substituted by hydrocarbon group with carbon number of 1-5 to be described later), allyl group, vinyl group, amino group, oxyamino group, hydrazide group or azide group, more preferably active ester group, active carbonate group, aldehyde group, maleimide group, oxyamino group, or amino group, particularly preferably active ester group, active carbonate group, aldehyde group, maleimide group, or oxyamino group.

In another preferred embodiment, the functional groups X can be classified into the following Group (II), Group (III), Group (IV), Group (V), Group (VI), and Group (VII).

Group (II): functional group capable of reacting with amino group of bio-related substance The groups represented by the following (a), (b), (c), (d), (e), (f), (g), (j) and (k) can be mentioned.

Group (III): functional group capable of reacting with mercapto group of bio-related substance The groups represented by the following (a), (b), (c), (d), (e), (f), (g), (h), (i), (j), (k) and (l) can be mentioned.

Group (IV): functional group capable of reacting with aldehyde group of bio-related substance The groups represented by the following (h), (m), (n) and (p) can be mentioned.

Group (V): functional group capable of reacting with carboxyl group of bio-related substance The groups represented by the following (h), (m), (n) and (p) can be mentioned.

Group (VI): functional group capable of reacting with unsaturated bond of bio-related substance The groups represented by the following (h), (m) and (o) can be mentioned.

Group (VII): functional group capable of reacting with azide group of bio-related substance The group represented by the following (l) can be mentioned.

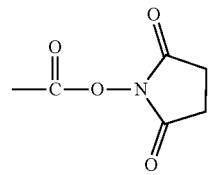
(a)

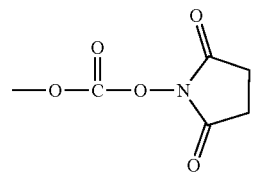
(b)

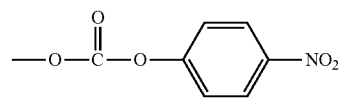
(c)

(d)

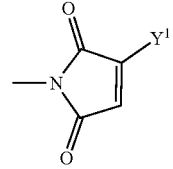
(e)

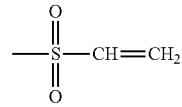
(f)

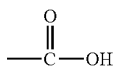
(g)

(h)

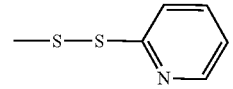
(i)

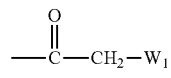
(j)

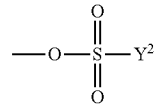
(k)

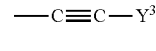
(l)

(m)

(n)

(o)

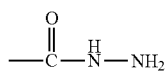

In functional group (j), $W_1$ in the formula is a halogen atom such as a chlorine atom (Cl), a bromine atom (Br) or an iodine atom (I), preferably Br or I, more preferably I.

In functional group (e) and functional group (l), $Y^1$ and $Y^3$ in the formula are each independently a hydrogen atom or a hydrocarbon group having 1 to 5 carbon atoms, preferably a hydrocarbon group having 1 to 5 carbon atoms. Specific examples of the hydrocarbon group having 1 to 5 carbon atoms include a methyl group, an ethyl group, a propyl group, an isopropyl group, a butyl group, a tertiary butyl group and the like, preferably a methyl group or an ethyl group.

In functional group (k), $Y^2$ in the formula is a hydrocarbon group having 1-10 carbon atoms and optionally containing a fluorine atom. Specifically, it is a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group, a 4-(trifluoromethoxy)phenyl group or the like, preferably a methyl group, a vinyl group, a 4-methylphenyl group, or a 2,2,2-trifluoroethyl group.

The active ester group is an ester group having an alkoxy group with high elimination ability. As the alkoxy group with high elimination ability, an alkoxy group induced from nitrophenol, N-hydroxysuccinimide, pentafluorophenol and the like can be mentioned. The active ester group is preferably an ester group having an alkoxy group induced from N-hydroxysuccinimide.

The active carbonate group is a carbonate group having an alkoxy group with high elimination ability. As the alkoxy group with high elimination ability, an alkoxy group induced from nitrophenol, N-hydroxysuccinimide, pentafluorophenol and the like can be mentioned. The active carbonate group is preferably a carbonate group having an alkoxy group induced from nitrophenol or N-hydroxysuccinimide.

The substituted maleimide group is a maleimide group in which a hydrocarbon group is bonded to one carbon atom of the double bond of the maleimide group. The hydrocarbon group is specifically a methyl group, an ethyl group, a propyl group, an isopropyl group, a butyl group, a tertiary butyl group and the like, preferably a methyl group or an ethyl group.

The substituted sulfonate group is a sulfonate group in which a hydrocarbon group which may contain a fluorine atom is bonded to a sulfur atom of the sulfonate group. As the hydrocarbon group which may contain a fluorine atom, specifically, a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group, a 4-(trifluoromethoxy) phenyl group and the like can be mentioned. It is preferably a methyl group, a vinyl group, a 4-methylphenyl group, or a 2,2,2-trifluoroethyl group.

Preferable examples of the branched degradable polyethylene glycol derivative of the formula (1) of the present invention include the following branched degradable polyethylene glycol derivative.

[Branched Degradable Polyethylene Glycol Derivative (1-1)]

A branched degradable polyethylene glycol derivative of the formula (1), wherein
 $k_1$ and $k_2$ are each independently 1-2;
 $j_1$ and $j_2$ are each independently 220-480;
 R is a hydrogen atom;
 Z is an oligopeptide of 2-8 residues consisting of neutral amino acids excluding cysteine (e.g., phenylalanine-glycine);
 X is selected from the group consisting of an active ester group (e.g., N-succinimidyloxycarbonyl group), an aldehyde group (e.g., N-(formylethyl)carbamoyl group), a carboxyl group, a maleimide group (e.g., N-(N-maleimidylethylcarbonylaminoethyl)carbamoyl group) and an amino group (e.g., N-(aminoethyl)carbamoyl group); and
 $L_1$ and $L_2$ are each independently an alkylene group (e.g., propylene group) optionally containing a secondary amino group and/or a carbonyl group.

The branched degradable polyethylene glycol derivative represented by the formula (1) can be produced, for example, by the following steps.

Reaction 1

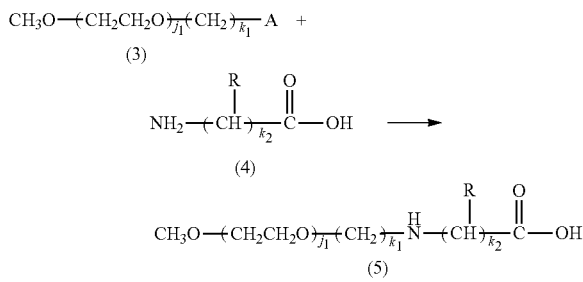

In reaction 1, A is a leaving group, and R, $j_1$, $k_1$, and $k_2$ are as defined above.

In the formula (3), A is a leaving group, and is not particularly limited as long as it is a leaving group having reactivity in the coupling reaction. For example, chloro group, bromo group, iodo group, mesylate group, tosylate group, chloromethanesulfonate group and the like can be mentioned.

In reaction 1, a polyethylene glycol derivative represented by the formula (3) and a compound represented by the formula (4) are subjected to a coupling reaction in an anhydrous solvent in the presence of a strong base catalyst to give a polyethylene glycol derivative represented by the formula (5).

The strong base catalyst in the aforementioned coupling reaction is not particularly limited as long as it is a strong base catalyst with which the reaction proceeds, and examples thereof include potassium hydroxide, sodium hydroxide, sodium methoxide, and sodium ethoxide.

The anhydrous solvent in the aforementioned coupling reaction is not particularly limited as long as it is a solvent that does not react with compounds represented by the formula (3) and the formula (4), and examples thereof include aprotic polar solvents such as tetrahydrofuran, acetonitrile, DMF, dichloromethane, chloroform and the like, and mixtures thereof.

Impurities by-produced in the reaction, or compounds that were not consumed and remain in the reaction, and strong base catalysts are preferably removed by purification. The purification is not particularly limited, and extraction, recrystallization, adsorption treatment, reprecipitation, column chromatography, supercritical extraction, and the like can be used for purification.

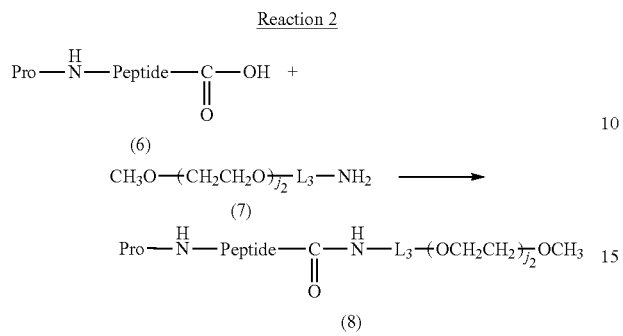

In reaction 2, Pro is a protecting group, Peptide is an oligopeptide, $L_3$ is a single bond or divalent spacer defined for the aforementioned $L_1$ and $L_2$, and $j_2$ is as defined above.

Pro in reaction 2 is a protecting group. A protecting group here is a component that prevents or inhibits the reaction of a particular chemically reactive functional group in a molecule under certain reaction conditions. Protecting groups vary depending on the kind of chemically reactive functional group to be protected, the conditions to be used and the presence of other functional group or protecting group in the molecule. Specific examples of the protecting group can be found in many general books, and they are described in, for example, "Wuts, P. G. M.; Greene, T. W. Protective Groups in Organic Synthesis, 4th ed.; Wiley-Interscience: New York, 2007". The functional group protected by a protecting group can be deprotected, that is, chemically reacted, using a reaction condition suitable for each protecting group, whereby the original functional group can be regenerated. Representative deprotection conditions for protecting groups are described in the aforementioned literature.

Reaction 2 is a process for bonding a carboxyl group of oligopeptide represented by the formula (6) with the N-terminal amino group protected by protecting group with an amino group of a polyethylene glycol derivative represented by the formula (7) in which one end is a methoxy group, by a condensation reaction to give polyethylene glycol derivative represented by the formula (8).

The protecting group of the N-terminal amino group of oligopeptide is not particularly limited. For example, an acyl protecting group and a carbamate protecting group can be mentioned, and a trifluoroacetyl group, a 9-fluorenylmethyloxycarbonyl group (Fmoc), a tert-butyloxycarbonyl group and the like can be specifically mentioned.

The condensation reaction is not particularly limited, and a reaction using a condensing agent is desirable. As the condensing agent, a carbodiimide condensing agent such as dicyclohexylcarbodiimide (DCC), 1-ethyl-3-(3-dimethylaminopropyl)carbodiimide hydrochloride (EDC) or the like may be used alone, or it may be used in combination with a reagent such as N-hydroxysuccinimide (NHS), 1-hydroxybenzotriazole (HOBt), 1-hydroxy-7-azabenzotriazole (HOAt) and the like. Also, a condensing agent with higher reactivity such as HATU, HBTU, TATU, TBTU, COMU, 4-(4,6-dimethoxy-1,3,5-triazin-2-yl)-4-methylmorpholinium chloride n hydrate (DMT-MM) and the like may be used. To promote the reaction, a base such as triethylamine, dimethylaminopyridine and the like may also be used.

Impurities by-produced in the reaction, or oligopeptides and condensing agents which were not consumed and remain in the reaction, and the like are preferably removed by purification. The purification is not particularly limited, and extraction, recrystallization, adsorption treatment, reprecipitation, column chromatography, supercritical extraction, and the like can be used for purification.

Deprotection 3

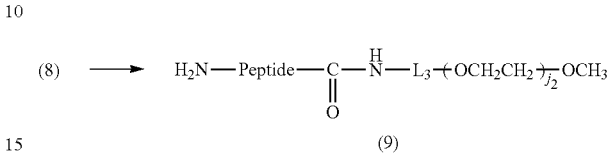

Peptide, $L_3$ and $j_2$ are as defined above.

In deprotection 3, the protecting group of the polyethylene glycol derivative represented by the formula (8) obtained in reaction 2 is removed to give a polyethylene glycol derivative represented by the formula (9). For the deprotection reaction, a conventionally-known method can be used. It is necessary to use conditions that do not cause degradation of oligopeptide or divalent spacer for $L_3$. This step can also be performed as a part of the step of reaction 2.

Impurities by-produced in the deprotection reaction, and the like are preferably removed by purification. The purification is not particularly limited, and extraction, recrystallization, adsorption treatment, reprecipitation, column chromatography, supercritical extraction, and the like can be used for purification.

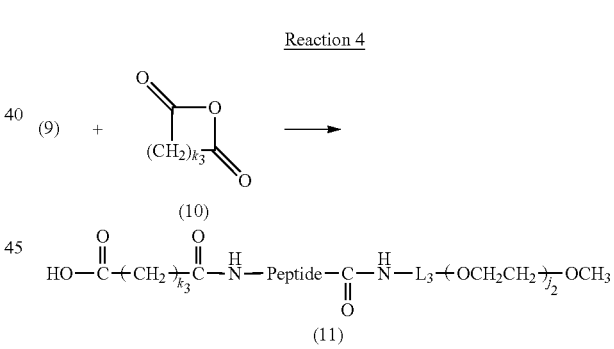

In reaction 4, $k_3$ is an integer of 1-6, and Peptide, $j_2$, and $L_3$ are as defined above.

In the formula (8), $k_3$ is an integer of 1-6, preferably 2-4.

In reaction 4, the terminal amino group of the polyethylene glycol derivative represented by the formula (9) obtained in deprotection 3 is converted to a carboxyl group by reacting with a compound represented by the formula (10) in the presence of a base catalyst.

Impurities by-produced in reaction 4, and the like are preferably removed by purification. The purification is not particularly limited, and extraction, recrystallization, adsorption treatment, reprecipitation, column chromatography, supercritical extraction, and the like can be used for purification.

Reaction 5

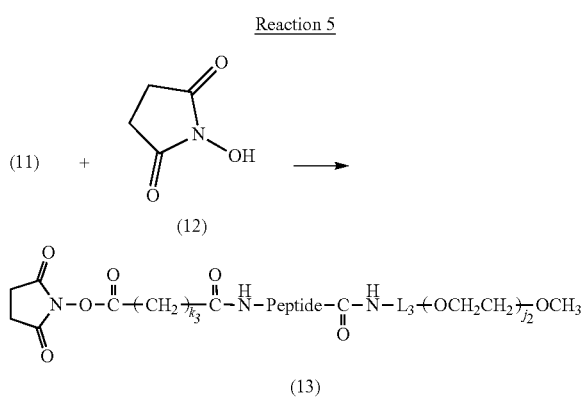

In reaction 5, Peptide, $L_3$, $k_3$, and $j_2$ are as defined above.

In reaction 5, the polyethylene glycol derivative represented by the formula (11) obtained in reaction 4 is reacted with a compound represented by the formula (12) in the presence of a base catalyst to give a polyethylene glycol derivative represented by the formula (13) into which an active ester group is introduced. This step can also be performed as a part of the step of reaction 4.

Reaction 6

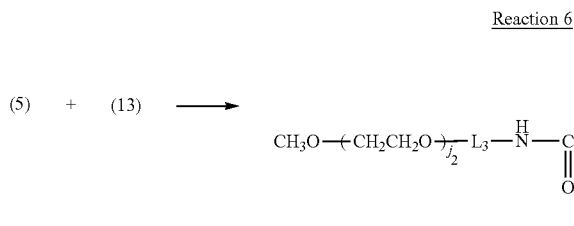

In reaction 6, Peptide, R, $L_3$, $j_1$, $j_2$, $k_1$, $k_2$, and $k_3$ are as defined above.

In reaction 6, an amino group of the polyethylene glycol derivative represented by the formula (5) and obtained in reaction 1 and an active ester group of the polyethylene glycol derivative represented by the formula (13) and obtained in reaction 5 are bonded by reaction to give a branched degradable polyethylene glycol derivative represented by the formula (14).

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

A typical example of the step of converting the terminal carboxyl group of the polyethylene glycol derivative represented by the formula (14) to other functional group is described below, but the conversion method is not limited thereto.

For example, when conversion of the terminal carboxyl group of the polyethylene glycol derivative represented by the formula (15) to a maleimide group is desired, a condensation reaction is performed with N-(2-aminoethyl)maleimide in the presence of a base catalyst, whereby the desired product can be obtained.

For example, when conversion of the terminal carboxyl group of the polyethylene glycol derivative represented by the formula (14) to an amino group is desired, it can be achieved by a condensation reaction with N-(9-H-fluoren-9-ylmethoxycarbonyl)-1,2-ethanediamine in the presence of a base catalyst, followed by a deprotection reaction.

These reaction reagents are low-molecular-weight reagents and have solubility vastly different from that of polyethylene glycol derivatives, which are high-molecular-weight polymers. Thus, they can be easily removed by general purification methods such as extraction and crystallization.

As a still another embodiment of the present invention, a branched degradable polyethylene glycol derivative of the following formula (2) is provided.

formula (2)

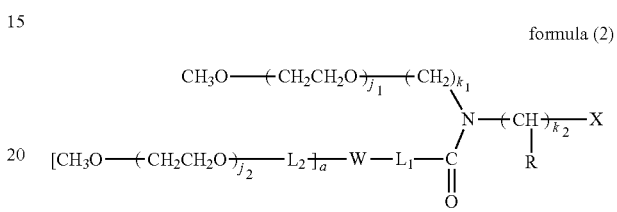

In the formula (2), $k_1$ and $k_2$ are each independently 1-12, $j_1$ and $j_2$ are each independently 45-950, R is a hydrogen atom, a substituted or unsubstituted alkyl group having 1-4 carbon atoms, a substituted aryl group, an aralkyl group or a heteroalkyl group, W is an oligopeptide of 5-47 residues having a symmetrical structure centered on glutamic acid or lysine, a is 2-8, X is a functional group capable of reacting with a bio-related substance, and $L_1$ and $L_2$ are each independently a single bond or a divalent spacer.

The total molecular weight of the polyethylene glycol derivative of the formula (2) of the present invention is generally 4,000-160,000, preferably 10,000-120,000, further preferably 20,000-80,000. In one preferred embodiment of the present invention, the total molecular weight of the polyethylene glycol derivative of the formula (2) of the present invention is not less than 20,000. The molecular weight here is a number average molecular weight (Mn).

In the formula (2), $k_1$ and $k_2$ are generally each independently 1-12, preferably each independently 1-6, further preferably each independently 1-2.

In the formula (2), $j_1$ and $j_2$ are each a repeating unit number of polyethylene glycol. Generally, they are each independently 45-950, preferably each independently 110-690, further preferably each independently 220-480.

W in the formula (2) is an oligopeptide of 5-47 residues, preferably 5-27 residues, more preferably 5-19 residues, having a symmetrical structure centered on glutamic acid or lysine, and is not particularly limited as long as it is an oligopeptide stable in the blood of living organisms and degraded by enzyme in cells. The amino acid constituting the oligopeptide preferably consists of neutral amino acid excluding cysteine, except for glutamic acid or lysine constituting the central portion. As used herein, the oligopeptide having a symmetrical structure centered on glutamic acid or lysine means a compound in which the same peptide is bonded to the α-position carboxyl group and the γ-position carboxyl group of glutamic acid or the α-position amino group and the ε-position amino group of lysine, and is an oligopeptide in which paired peptides centered on glutamic acid or lysine have a symmetrical structure. The composition ratio of the number of neutral amino acids and glutamic acids or lysine in the oligopeptide (number of neutral amino acids/number of glutamic acids) is generally 2-10, preferably 2-8, further preferably 2-6. The amino acid constituting W is basically of an L type.

Particularly preferred embodiments of W are shown in the following Group (VIII).

Group (VIII):

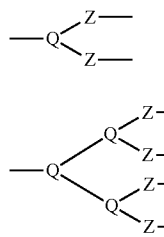

(w1)

(w2)

wherein Q is a glutamic acid residue or lysine residue, and Z is a degradable oligopeptide of 2-5 residues consisting of neutral amino acids excluding cysteine.

In the formula (2), a is the number of polyethylene glycol chains bonded to oligopeptide for W. Generally, it is 2-8, preferably 2 or 4 or 8, further preferably 2 or 4.

Preferred embodiments of R, X, $L_1$, $L_2$ and Z in (w1)-(w2) are as described in the aforementioned formula (1).

One of the preferred embodiments of the formula (2) is a 3-branched degradable polyethylene glycol derivative represented by the following formula (15) wherein W is w1, and a=2:

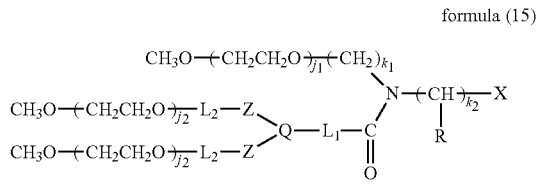

formula (15)

wherein Q, Z, R, $k_1$, $k_2$, $j_1$, $j_2$, X, $L_1$ and $L_2$ are as defined above.

One of the preferred embodiments of the formula (2) is a 5-branched degradable polyethylene glycol derivative represented by the following formula (16) wherein W is w2, and a=4:

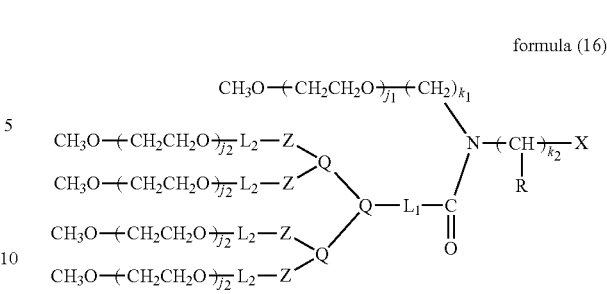

formula (16)

wherein Q, R, Z, $k_1$, $k_2$, $j_1$, $j_2$, X, $L_1$ and $L_2$ are as defined above.

Preferred examples of the branched degradable polyethylene glycol derivative of the formula (2) of the present invention include the following branched degradable polyethylene glycol derivative.

[Branched Degradable Polyethylene Glycol Derivative (2-1)]

A branched degradable polyethylene glycol derivative of the formula (2), wherein
$k_1$ and $k_2$ are each independently 1-2;
$j_1$ and $j_2$ are each independently 220-480;
R is a hydrogen atom;
W is an oligopeptide of 5-9 residues having a symmetrical structure centered on glutamic acid or lysine (e.g., glycine-phenylalanine-glutamic acid-phenylalanine-glycine);
a is 2 or 4;
X is a carboxyl group; and
$L_1$ and $L_2$ are each independently an alkylene group (e.g., propylene group, pentylene group) optionally containing an ether bond, a secondary amino group and/or a carbonyl group.

The branched degradable polyethylene glycol derivative of the present invention wherein Q is a glutamic acid residue can be produced, for example, by the following steps.

Reaction 7

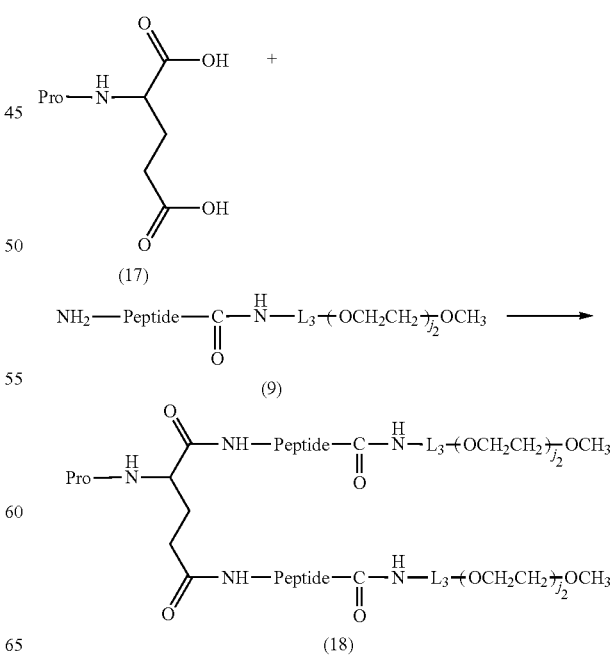

In reaction 7, Pro, Peptide, $L_3$ and $j_2$ are as defined above.

In reaction 7, the amino group of the polyethylene glycol derivative represented by the formula (9) obtained in deprotection 3 and the two carboxyl groups of the glutamic acid derivative represented by the formula (17) whose amino group is protected by a protecting group are bonded by a condensation reaction to give the branched polyethylene glycol derivative represented by the formula (18) having a structure in which two degradable polyethylene glycol chains are connected by a glutamic acid residue.

Similar to the aforementioned reaction 2, a reaction using a condensing agent is desirable and to promote the reaction, a base such as triethylamine, dimethylaminopyridine and the like may also be used.

The protecting group of amino group of glutamic acid is not particularly limited and for example, an acyl protecting group and a carbamate protecting group can be mentioned, and a trifluoroacetyl group, a 9-fluorenylmethyloxycarbonyl group, a tert-butyloxycarbonyl group and the like can be specifically mentioned.

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

Deprotection 8

(18) ⟶

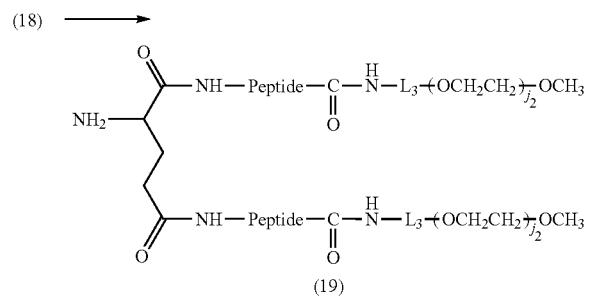

(19)

In deprotection 8, Peptide, $L_3$ and $j_2$ are as defined above.

Deprotection 8 is a process for removing the protecting group of polyethylene glycol derivative represented by the formula (18) and obtained in reaction 7 to give polyethylene glycol derivative represented by the formula (19). The reaction and purification can be performed under the same conditions as in the aforementioned deprotection 3.

As a method for removing polyethylene glycol impurities having different molecular weight and different functional group from polyethylene glycol derivative represented by the formula (19), the purification techniques described in JP-A-2014-208786, JP-A-2011-79934 can be used.

Reaction 9

(17) + (19) ⟶ 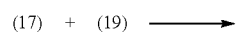

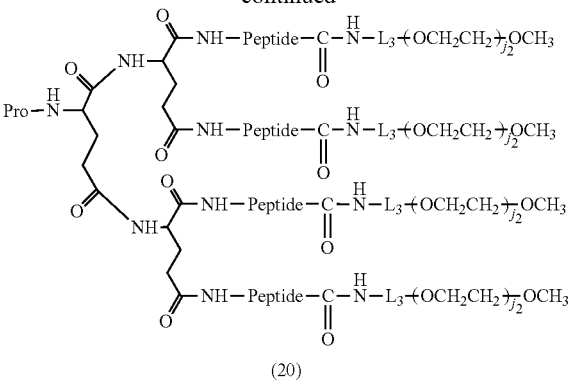

(20)

In reaction 9, Pro, Peptide, $L_3$ and $j_2$ are as defined above.

In reaction 9, the amino group of the polyethylene glycol derivative represented by the formula (19) obtained in deprotection 8 and the two carboxyl groups of the glutamic acid derivative represented by the formula (17) whose amino group is protected by a protecting group are bonded by a condensation reaction to give the branched polyethylene glycol derivative represented by the formula (20) having a structure in which four degradable polyethylene glycol chains are connected by a glutamic acid residue. The reaction and purification can be performed under the same conditions as in the aforementioned reaction 2.

Deprotection 10

(20) ⟶

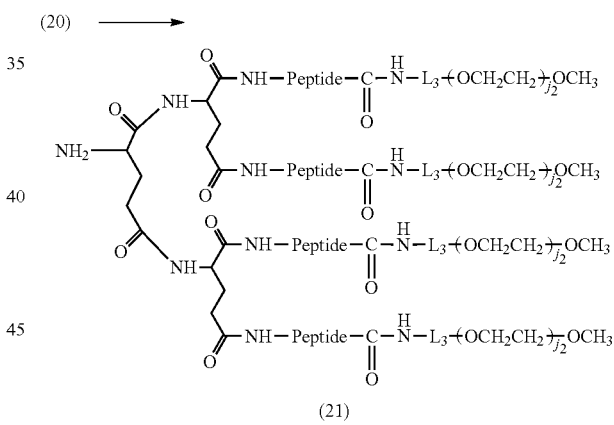

(21)

In deprotection 10, Peptide, $L_3$ and $j_2$ are as defined above.

Deprotection 10 is a process for removing the protecting group of polyethylene glycol derivative represented by the formula (20) obtained in reaction 9 to give polyethylene glycol derivative represented by the formula (21). The reaction and purification can be performed under the same conditions as in the aforementioned deprotection 8. This step can also be performed in a series of reaction 9.

Reaction 11

(19) + 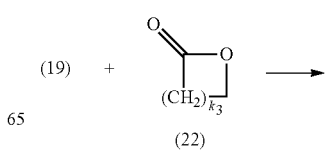 ⟶

(22)

-continued

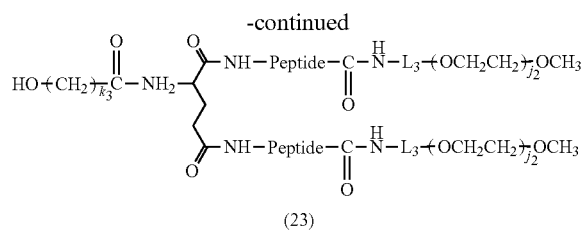

(23)

In reaction 11, Peptide, $L_3$, $j_2$ and $k_3$ are as defined above.

In reaction 11, a terminal amino group of the 2-branched polyethylene glycol derivative represented by the formula (19) and obtained in deprotection 8 is converted to a hydroxyl group by reacting with a compound represented by the formula (22) in the presence of a base catalyst to give a 2-branched polyethylene glycol derivative represented by the formula (23). The reaction and purification can be performed under the same conditions as in the aforementioned reaction 4.

Furthermore, using the 4-branched polyethylene glycol derivative represented by the formula (21) and obtained in deprotection 10 instead of the 2-branched polyethylene glycol derivative represented by the formula (19) in reaction 11 as a starting material, a 4-branched polyethylene glycol derivative represented by the following formula (24) can be obtained.

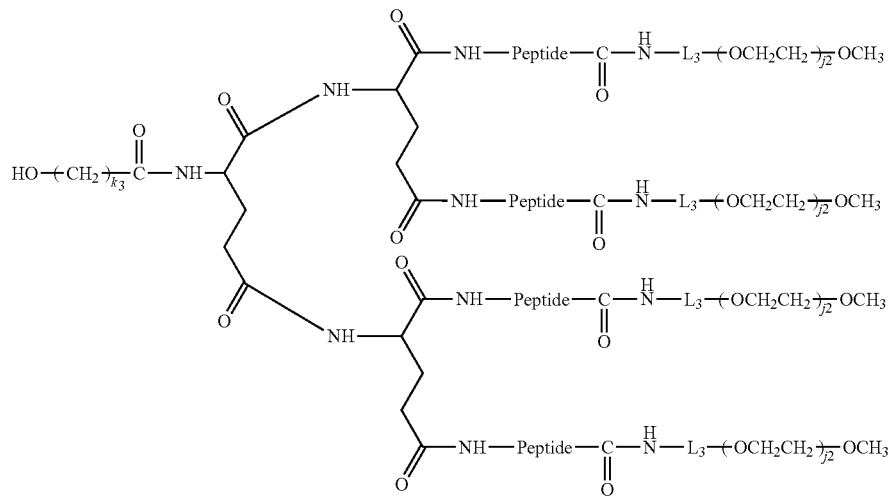

(24)

In the formula (24), Peptide, $L_3$, $j_2$ and $k_3$ are as defined above.

Reaction 12

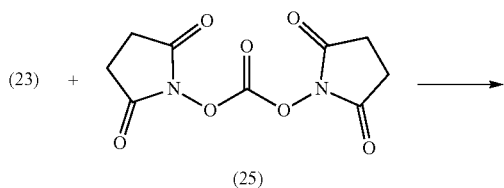

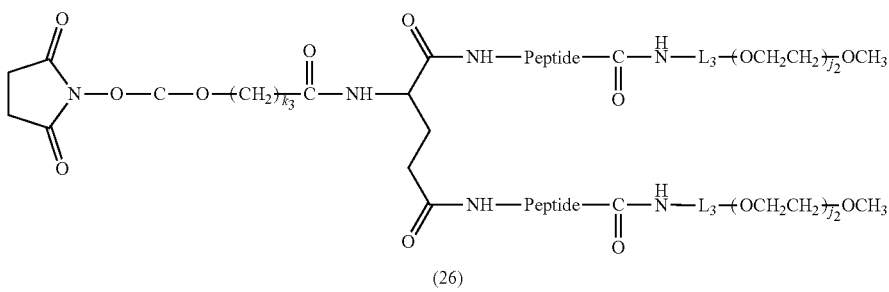

(26)

In reaction 12, Peptide, $L_3$, $j_2$ and $k_3$ are as defined above.

In reaction 12, a hydroxyl group of the 2-branched polyethylene glycol derivative represented by the formula (23) and obtained in reaction 11 is reacted with a compound represented by the formula (25) to give a 2-branched polyethylene glycol derivative represented by the formula (26) into which an active carbonate group has been introduced. This step can also be performed as a part of the step of reaction 11, and the reaction and purification can be performed under the same conditions as in the aforementioned reaction 5.

Furthermore, using the 4-branched polyethylene glycol derivative represented by the formula (24) instead of the 2-branched polyethylene glycol derivative represented by the formula (23) in reaction 12 as a starting material, a 4-branched polyethylene glycol derivative represented by the following formula (27) can be obtained.

In reaction 13, Peptide, R, $L_3$, $j_1$, $j_2$, $k_1$, $k_2$ and $k_3$ are as defined above.

In reaction 13, an amino group of the polyethylene glycol derivative represented by the formula (5) and obtained in reaction 1 and an active ester group of the polyethylene glycol derivative represented by the formula (26) and obtained in reaction 12 are bonded by reaction to give a 3-branched degradable polyethylene glycol derivative represented by the formula (28), and the reaction and purification can be performed under the same conditions as in the aforementioned reaction 6.

Furthermore, using the 4-branched polyethylene glycol derivative represented by the formula (27) instead of the 2-branched polyethylene glycol derivative represented by

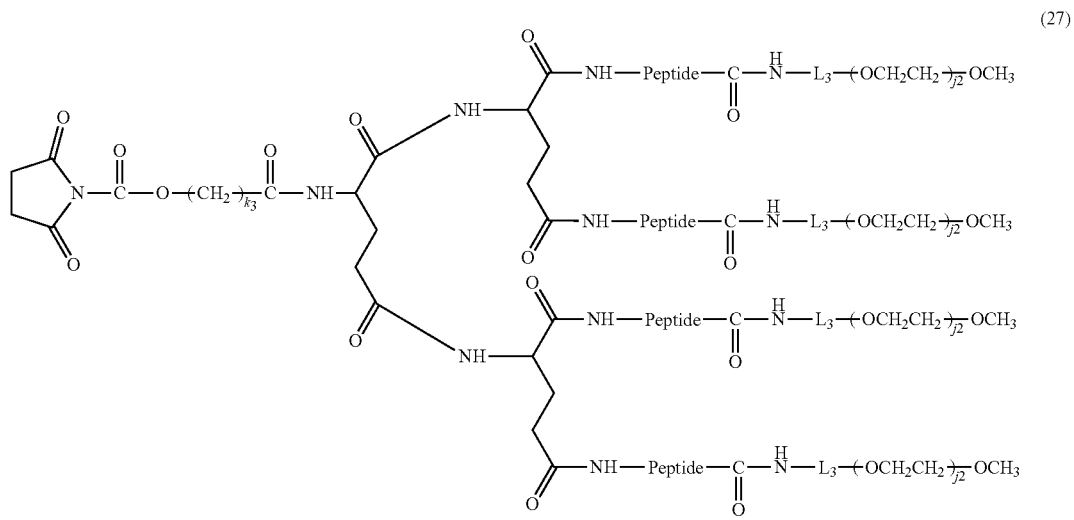

In the formula (27), Peptide, $L_3$, $j_2$ and $k_3$ are as defined above.

Reaction 13 the formula (26) in reaction 13 as a starting material, a 5-branched polyethylene glycol derivative represented by the following formula (29) can be obtained.

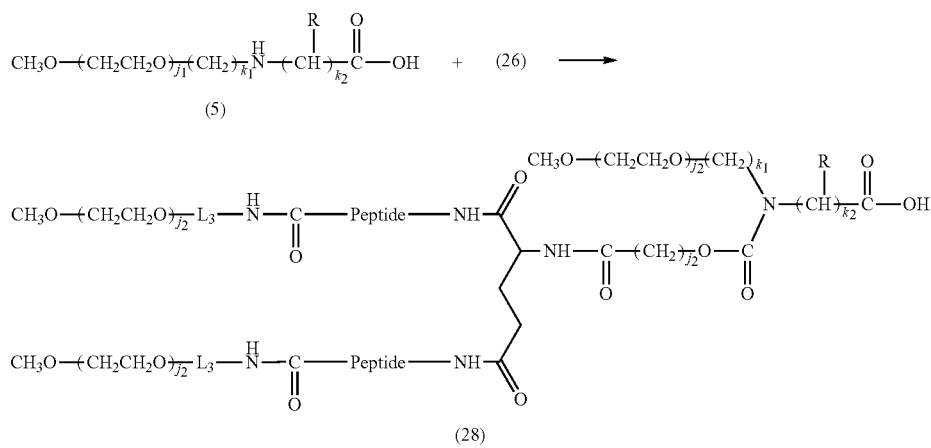

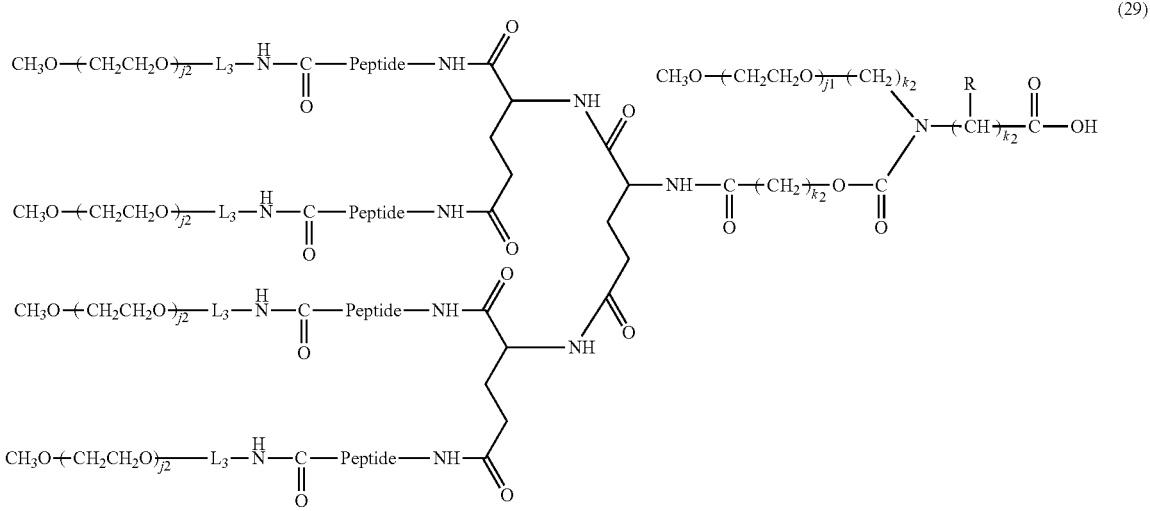

(29)

In the formula (29), Peptide, R, $L_3$, $j_1$, $j_2$, $k_1$, $k_2$ and $k_3$ are as defined above.

A typical example of the step of converting the terminal carboxyl group of the branched polyethylene glycol derivative represented by the formula (28) or the formula (29) to other functional group is described below, but the conversion method is not limited thereto.

For example, when conversion of the terminal carboxyl group of the branched polyethylene glycol derivative represented by the formula (28) or the formula (29) to a maleimide group is desired, a condensation reaction is performed with N-(2-aminoethyl)maleimide in the presence of a base catalyst, whereby the desired product can be obtained.

For example, when conversion of the terminal carboxyl group of the polyethylene glycol derivative represented by the formula (28) or the formula (29) to an amino group is desired, it can be achieved by a condensation reaction with N-(9-H-fluoren-9-ylmethoxycarbonyl)-1,2-ethanediamine in the presence of a base catalyst, followed by a deprotection reaction.

Since these reaction reagents are low-molecular-weight reagents and have solubility vastly different from that of polyethylene glycol derivatives, which are high-molecular-weight polymers, they can be easily removed by general purification methods such as extraction and crystallization.

The branched degradable polyethylene glycol obtained through the above steps is required to be stable in blood and have the property of being degraded only in cells. To properly evaluate the property, for example, the following test is performed, based on which the stability in blood and degradability in cells of the branched degradable polyethylene glycol can be evaluated.

In consideration of the influence of the kind of the functional group of the polyethylene glycol derivative in these evaluations, all the evaluation samples used for the tests were polyethylene glycol derivatives having one amino group.

The test method for evaluating the stability of branched degradable polyethylene glycol derivative in blood is not particularly limited. For example, a test using serum of mouse, rat, human or the like can be mentioned. Specifically, a polyethylene glycol derivative is dissolved in serum to a concentration of 1-10 mg/mL, incubated at 37° C. for 96 hr, the polyethylene glycol derivative contained in the serum is recovered and GPC is measured to evaluate the degradation rate. The degradation rate is calculated from the peak area % of the GPC main fraction of the polyethylene glycol derivative before the stability test and the peak area % of the GPC main fraction of the polyethylene glycol derivative after the stability test. Specifically, the following formula is used.

degradation rate=(peak area % before test−peak area % after test)÷peak area % before test×100

For example, when the peak area % of the GPC main fraction of the branched degradable polyethylene glycol derivative before the stability test is 95% and the peak area % of the GPC main fraction after the stability test is 90%, the degradation rate is calculated as follows.

degradation rate=(95−90)÷95×100=5.26(%)

When the branched degradable polyethylene glycol derivative is degraded in blood, the desired half-life in blood cannot be achieved. Thus, in the stability test, the degradation rate after 96 hr is preferably not more than 10%, more preferably not more than 5%.

The test method for evaluating the intracellular degradability of the branched degradable polyethylene glycol derivative is not particularly limited. For example, a test including culturing cells in a medium containing a branched degradable polyethylene glycol derivative and the like can be mentioned. The cells and medium to be used here are not particularly limited. Specifically, a polyethylene glycol derivative is dissolved in RPMI-1640 medium to a concentration of 1-20 mg/mL, macrophage cells RAW264.7 are cultured in the medium at 37° C. for 96 hr, the polyethylene glycol derivative in the cells is recovered, and GPC is measured to evaluate the degradation rate. The degradation rate is calculated using the peak area % of the GPC main fraction of the polyethylene glycol derivative before and after the test, as in the stability test.

For example, when the peak area % of the GPC main fraction of the branched degradable polyethylene glycol derivative before the degradability test is 95% and the peak area % of the GPC main fraction after the test is 5%, the degradation rate is calculated as follows.

degradation rate=(95−5)÷95×100=94.7(%)

When the branched degradable polyethylene glycol derivative is not efficiently degraded in cells, the desired suppression of cell vacuoles cannot be achieved. Thus, in the degradability test, the degradation rate after 96 hr is preferably not less than 90%, more preferably not less than 95%.

Non-patent literature 2 describes that vacuolization of cells by high-molecular-weight polyethylene glycol is related to accumulation of polyethylene glycol in tissue. The test method for evaluating accumulation of a degradable polyethylene glycol derivative in cells is not particularly limited, and evaluation can be made by the above-mentioned intracellular degradability.

EXAMPLE

The present invention is explained in more detail in the following based on Examples; however, the present invention is not limited to the following Examples.

$^1$H-NMR obtained in the following Examples was obtained from JNM-ECP400 or JNM-ECA600 manufactured by JEOL Datam Co., Ltd. A φ5 mm tube was used for the measurement, and $D_2O$ or $CDCl_3$ and $d_6$-DMSO containing tetramethylsilane (TMS) as an internal standard substance were used as deuterated solvents. The molecular weight and purity of terminal functional group of the obtained polyethylene glycol derivative were calculated using liquid chromatography (GPC and HPLC). As a liquid chromatography system, "HLC-8320GPC EcoSEC" manufactured by Tosoh Corporation was used for GPC, and "ALLIANCE" manufactured by WATERS was used for HPLC.

Example 1

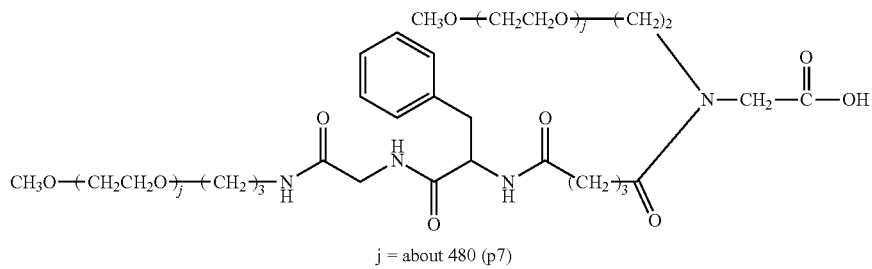

j = about 480 (p7)

Example 1-1

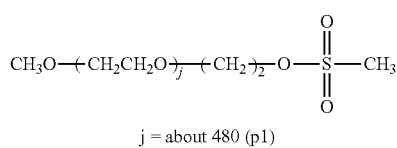

j = about 480 (p1)

"SUNBRIGHT MEH-20T" having average molecular weight=20,000, manufactured by NOF CORPORATION (10 g) was dissolved in toluene (40 g), and the solution was dehydrated by refluxing at 110° C. for 1 hr, cooled to 40° C., triethylamine (80 mg) and methanesulfonyl chloride (84 mg) were added, and the mixture was reacted at 40° C. for 3 hr. After completion of the reaction, the mixture was diluted with toluene (100 g), hexane (100 g) was added, and the mixture was stirred at room temperature for 30 min. The resultant product was precipitated and suction filtered using 5A filter paper. The precipitate was recovered, dissolved in ethyl acetate (200 g), hexane (100 g) was added, and the mixture was stirred at room temperature for 15 min. The resultant product was precipitated and suction filtered using 5A filter paper. The precipitate was recovered, washed with hexane (100 g), suction filtered using 5A filter paper, and dried in vacuo to give the compound (p1). yield 8.9 g.

$^1$H-NMR (CDCl$_3$): 3.08 ppm (s, 3H, —O—SO$_2$—C$\underline{H}_3$) 3.38 ppm (s, 3H, —O—CH$_2$—CH$_2$—(O—CH$_2$—CH$_2$)$_j$—O—C$\underline{H}_3$), 3.64 ppm (m, about 1,900H, —O—CH$_2$—CH$_2$—(O—C$\underline{H}_2$—C$\underline{H}_2$)$_j$—O—CH$_3$)

Example 1-2

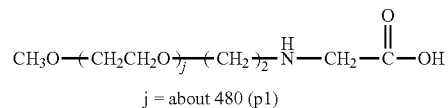

j = about 480 (p1)

Glycine hydrochloride (5 g) was dissolved in ion exchange water (50 g). NaOH (3.0 g) was added to the aforementioned glycine aqueous solution to adjust the pH to 10.8. Thereafter, the compound (p1) (8 g) obtained in Example 1-1 was added to the aforementioned aqueous solution, and the solution was reacted at 40° C. for 72 hr. After the reaction, the reaction mixture was neutralized with hydrochloric acid solution to pH about 7. After neutralization, chloroform (50 g) was added, the mixture was stirred at room temperature for 15 min, and the organic layer was recovered. The organic layer was concentrated, redissolved in ethyl acetate (100 g), hexane (50 g) was added, and the mixture was stirred at room temperature for 15 min. The resultant product was precipitated and suction filtered using 5A filter paper. The precipitate was recovered, washed with hexane (50 g), suction filtered using 5A filter paper, and dried in vacuo to give the compound (p2). yield 6.8 g.

$^1$H-NMR (d$_6$-DMSO): 2.72 ppm (t, 2H, —NH—C$\underline{H}_2$—CH$_2$—(O—CH$_2$—CH$_2$)$_j$—O—C$\underline{H}_3$) 3.24 ppm (s, 3H, —NH—CH$_2$—CH$_2$—(O—CH$_2$—CH$_2$)$_j$—O—C$\underline{H}_3$), 3.48 ppm (m, about 1,900H, —C$\underline{H}_2$—NH—CH$_2$—C$\underline{H}_2$—(O—C$\underline{H}_2$—C$\underline{H}_2$)$_j$—O—CH$_3$), 5.52 ppm (broad, 1H, —N$\underline{H}$—CH$_2$—COOH)

Example 1-3

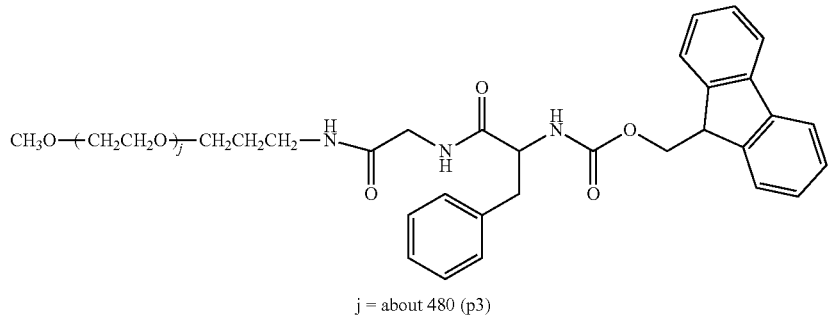

j = about 480 (p3)

L-phenylalanyl-glycine with the N-terminal protected by a 9-fluorenylmethyloxycarbonyl group (Fmoc group) (Fmoc-Phe-Gly) (0.44 g) and "SUNBRIGHT MEPA-20T" (10 g) having average molecular weight=20,000, manufactured by NOF CORPORATION were dissolved in acetonitrile (40 g) added thereto. Thereafter, diisopropylethylamine (1.56 g) and 4-(4,6-dimethoxy-1,3,5-triazin-2-yl)-4-methylmorpholinium chloride n hydrate (DMT-MM) (0.22 g) were added, and the mixture was reacted at room temperature under a nitrogen atmosphere for 1 hr. After completion of the reaction, the mixture was concentrated at 40° C., toluene (100 g) was added to the concentrate, and the mixture was uniformly stirred, and suction filtered using 5A filter paper. To the obtained filtrate was added hexane (100 g), and the mixture was stirred at room temperature for 15 min. The resultant product was precipitated and suction filtered using 5A filter paper. The precipitate was recovered, dissolved again in toluene (100 g), hexane (100 g) was added, and the mixture was stirred at room temperature for 15 min. The resultant product was precipitated and suction filtered using 5A filter paper. The precipitate was recovered, washed with hexane (50 g), suction filtered using 5A filter paper, and dried in vacuo to give the above-mentioned compound (p3). yield 8.6 g.

$^1$H-NMR ($d_6$-DMSO): 1.62 ppm (m, 2H, —CO—NH—CH$_2$—<u>CH$_2$</u>—CH$_2$—O—(CH$_2$—CH$_2$—O)j-CH$_3$), 2.80 ppm (m, 1H, —NH—CO—CH—<u>CH$_2$</u>—C$_6$H$_5$), 3.04 ppm (m, 1H, —NH—CO—CH—<u>CH$_2$</u>—C$_6$H$_5$), 3.10 ppm (m, 2H, —CO—NH—<u>CH$_2$</u>—CH$_2$—CH$_2$—O—(CH$_2$—CH$_2$—O)j-CH$_3$), 3.24 ppm (s, 3H, —CO—NH—CH$_2$—CH$_2$—CH$_2$—O—(CH$_2$—CH$_2$—O)j-<u>CH$_3$</u>), 3.48 ppm (m, about 1,900H, —CO—NH—CH$_2$—CH$_2$—CH$_2$—O—(<u>CH$_2$</u>—<u>CH$_2$</u>—O)j-CH$_3$), 4.20 ppm (m, 4H), 7.33 ppm (m, 9H), 7.66 ppm (m, 4H, Ar), 7.88 ppm (d, 2H, Ar), 8.27 ppm (t, 1H)

Example 1-4

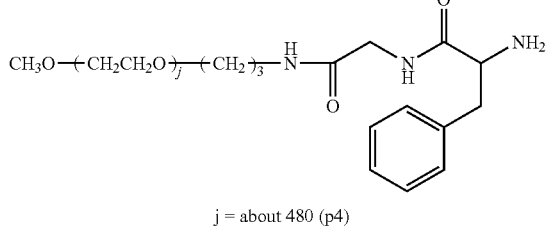

j = about 480 (p4)

Compound (p3) (8.0 g) was dissolved in acetonitrile (40 g). Thereafter, piperidine (0.86 g) was added, and the mixture was reacted at room temperature under a nitrogen atmosphere for 2 hr. After completion of the reaction, 20% brine (80 g) was added, and the mixture was washed by stirring at room temperature for 15 min. The organic layer and the aqueous layer were separated, to the organic layer was added again 20% brine (80 g), the mixture was washed by stirring at room temperature for 15 min, and the organic layer was recovered. The obtained organic layer was concentrated at 40° C., toluene (200 g) and magnesium sulfate (10 g) were added to the concentrate, and the mixture was dehydrated by stirring at room temperature for 30 min, and suction filtered using 5A filter paper. To the obtained filtrate was added hexane (100 g) and the mixture was stirred at room temperature for 15 min. The resultant product was precipitated and suction filtered using 5A filter paper. The precipitate was recovered, washed with hexane (100 g), suction filtered using 5A filter paper, and dried in vacuo to give the above-mentioned compound (p4). yield 7.2 g.

HPLC: amine purity 92%.

$^1$H-NMR ($d_6$-DMSO): 1.62 ppm (m, 2H, —CO—NH—CH$_2$—<u>CH$_2$</u>—CH$_2$—O—(CH$_2$—CH$_2$—O)j-CH$_3$), 1.64 ppm (broad, 1H), 2.59 ppm (dd, 1H, —NH—CO—CH—<u>CH$_2$</u>—C$_6$H$_5$), 2.98 ppm (dd, 1H, —NH—CO—CH—<u>CH$_2$</u>—C$_6$H$_5$), 3.10 ppm (q, 2H, —CO—NH—<u>CH$_2$</u>—CH$_2$—CH$_2$—O—(CH$_2$—CH$_2$—O)j-CH$_3$), 3.24 ppm (s, 3H, —CO—NH—CH$_2$—CH$_2$—CH$_2$—O—(CH$_2$—CH$_2$—O)j-<u>CH$_3$</u>), 3.48 ppm (m, about 1,900H, —CO—NH—CH$_2$—CH$_2$—O—(<u>CH$_2$</u>—<u>CH$_2$</u>—O)j-CH$_3$), 7.24 ppm (m, 6H, —NH—CO—CH—CH$_2$—<u>C$_6$H$_5$</u>, —NH—), 7.73 ppm (t, 1H), 8.12 ppm (broad, 1H)

Example 1-5

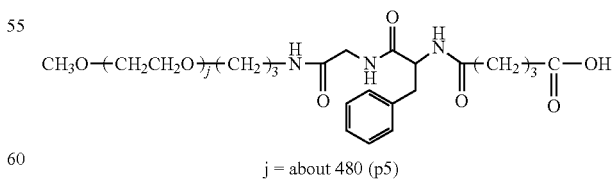

j = about 480 (p5)

The compound (p4) (6.0 g) obtained in Example 1-4, sodium acetate (49 mg), and glutaric anhydride (51 mg) were dissolved in toluene (25 g), and the mixture was reacted under a nitrogen atmosphere at 40° C. for 7 hr. After completion of the reaction, the mixture was diluted with toluene (20 g), suction filtered using 5A filter paper, to the obtained filtrate was added hexane (30 g), and the mixture was stirred at room temperature for 15 min. The resultant product was precipitated and suction filtered using 5A filter paper. The precipitate was recovered, the obtained precipitate was dissolved in ethyl acetate (100 g), hexane (50 g) was added, and the mixture was stirred at room temperature for 15 min. The resultant product was precipitated and suction filtered using 5A filter paper. The precipitate was recovered, washed with hexane (50 g), suction filtered using 5A filter paper, and dried in vacuo to give the above-mentioned compound (p5). yield 4.8 g.

$^1$H-NMR (d$_6$-DMSO): 1.62 ppm (m, 2H, —CO—NH—CH$_2$—CH$_2$—CH$_2$—O—(CH$_2$—CH$_2$—O)j-CH$_3$), 1.64 ppm (broad, 1H), 2.05 ppm (dd, 2H, —NH—CO—CH$_2$—CH$_2$—CH$_2$—COOH) 2.30 ppm (m, 4H, —NH—CO—CH$_2$—CH$_2$—CH$_2$—COOH), 2.59 ppm (dd, 1H, —NH—CO—CH—CH$_2$—C$_6$H$_5$), 2.98 ppm (dd, 1H, —NH—CO—CH—CH$_2$—C$_6$H$_5$), 3.10 ppm (q, 2H, —CO—NH—CH$_2$—CH$_2$—CH$_2$—O—(CH$_2$—CH$_2$—O)j-CH$_3$), 3.24 ppm (s, 3H, —CO—NH—CH$_2$—CH$_2$—CH$_2$—O—(CH$_2$—CH$_2$—O)j-CH$_3$), 3.48 ppm (m, about 1,900H, —CO—NH—CH$_2$—CH$_2$—CH$_2$—O—(CH$_2$—CH$_2$—O)j-CH$_3$), 7.24 ppm (m, 6H, —NH—CO—CH—CH$_2$—C$_6$H$_5$, —NH—), 7.73 ppm (t, 1H), 8.12 ppm (broad, 1H)

Example 1-6

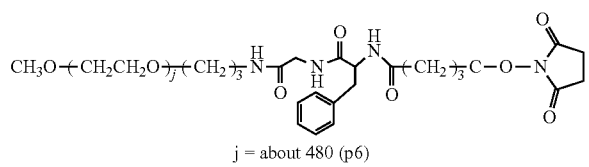

j = about 480 (p6)

The compound (p5) (4.5 g) obtained in Example 1-5 and N-hydroxysuccinimide (103 mg) were dissolved in toluene (25 g). Thereafter, dicyclohexylcarbodiimide (139 mg) was added, and the mixture was reacted at 40° C. under a nitrogen atmosphere for 3 hr. After completion of the reaction, toluene (50 g) was added for dilution, and the mixture was suction filtered using 5A filter paper. To the obtained filtrate was added hexane (50 g), and the mixture was stirred at room temperature for 15 min. The resultant product was precipitated and suction filtered using 5A filter paper. The precipitate was recovered, dissolved in ethyl acetate (100 g), hexane (50 g) was added, and the mixture was stirred at room temperature for 15 min. The resultant product was precipitated and suction filtered using 5A filter paper. The precipitate was recovered, washed with hexane (50 g), suction filtered using 5A filter paper, and dried in vacuo to give the above-mentioned compound (p6). yield 3.5 g.

active ester purity 98% ($^1$H-NMR).

$^1$H-NMR (d$_6$-DMSO): 1.62 ppm (m, 2H, —CO—NH—CH$_2$—CH$_2$—CH$_2$—O—(CH$_2$—CH$_2$—O)j-CH$_3$), 1.64 ppm (broad, 1H), 2.05 ppm (dd, 2H, —NH—CO—CH$_2$—CH$_2$—CH$_2$—CO—), 2.30 ppm (m, 4H, —NH—CO—CH$_2$—CH$_2$—COO—), 2.59 ppm (dd, 1H, —NH—CO—CH—CH$_2$—C$_6$H$_5$), 2.72 ppm (s, 4H, —CO—CH$_2$—CH$_2$—CO—), 2.98 ppm (dd, 1H, —NH—CO—CH—CH$_2$—C$_6$H$_5$), 3.10 ppm (q, 2H, —CO—NH—CH$_2$—CH$_2$—CH$_2$—O—(CH$_2$—CH$_2$—O)j-CH$_3$), 3.24 ppm (s, 3H, —CO—NH—CH$_2$—CH$_2$—CH$_2$—O—(CH$_2$—CH$_2$—O)j-CH$_3$), 3.48 ppm (m, about 1,900H, —CO—NH—CH$_2$—CH$_2$—CH$_2$—O—(CH$_2$—CH$_2$—O)j-CH$_3$), 7.24 ppm (m, 6H, —NH—CO—CH—CH$_2$—C$_6$H$_5$, —NH—), 7.73 ppm (t, 1H), 8.12 ppm (broad, 1H)

Example 1-7

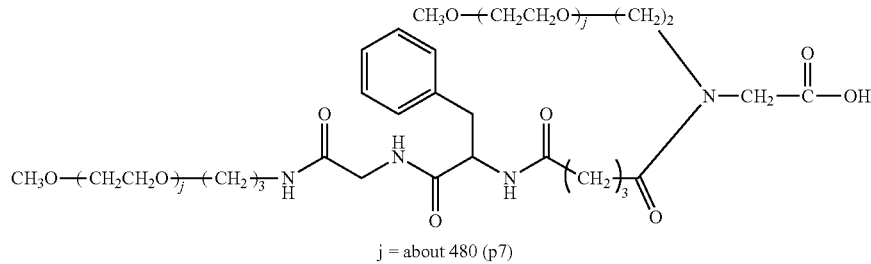

j = about 480 (p7)

The compound (p2) (3.0 g) obtained in Example 1-2 and the compound (p6) (3.0 g) obtained in Example 1-6 were dissolved in dichloromethane (60 g), triethylamine (95 mg) was added, and the mixture was reacted at room temperature for 8 hr. After the reaction, 20% brine (50 g) was added, and the mixture was stirred at room temperature for 15 min. The reaction mixture was washed, and the organic layer was recovered. To the organic layer was added magnesium sulfate (10 g), and the mixture was stirred at room temperature for 15 min, and suction filtered using 5A filter paper. The obtained filtrate was concentrated, the concentrate was dissolved in ethyl acetate (100 g), hexane (50 g) was added, and the mixture was stirred at room temperature for 15 min. The resultant product was precipitated and suction filtered using 5A filter paper. The precipitate was recovered, dissolved again in ethyl acetate (100 g), hexane (50 g) was added, and the mixture was stirred at room temperature for 15 min. The resultant product was precipitated and suction filtered using 5A filter paper. The precipitate was recovered, washed with hexane (50 g) containing 2,6-di-tert-butyl-p-cresol (BHT) (10 mg), suction filtered using 5A filter paper, and dried in vacuo to give the above-mentioned compound (p7). yield 4.2 g.

HPLC: The carboxylic acid purity was 95%.

$^1$H-NMR (d$_6$-DMSO): 1.62 ppm (m, 2H, CO—NH—CH$_2$—CH$_2$—CH$_2$—O—(CH$_2$—CH$_2$—O)j-CH$_3$), 1.64 ppm (broad, 1H), 2.05 ppm (dd, 2H, —NH—CO—CH$_2$—CH$_2$—CH$_2$—CO—), 2.30 ppm (m, 4H, —NH—CO—CH$_2$—CH$_2$—CH$_2$—CO—), 2.59 ppm (dd, 1H, —NH—CO—CH—CH$_2$—C$_6$H$_5$), 2.98 ppm (dd, 1H, —NH—CO—CH—CH$_2$—C$_6$H$_5$), 3.24 ppm (s, 3H, —NH—CH$_2$—CH$_2$—(O—CH$_2$—CH$_2$)j-O—CH$_3$), 3.48 ppm (m, about 3,800H, —CH$_2$—NH—CH$_2$—CH$_2$—(O—CH$_2$—CH$_2$)j-O—CH$_3$), 4.61 ppm (—CH$_2$—COOH), 7.24 ppm (m, 6H, —NH—CO—CH—CH$_2$—C$_6$H$_5$, —NH—), 7.73 ppm (t, 1H), 8.12 ppm (broad, 1H))

Example 2

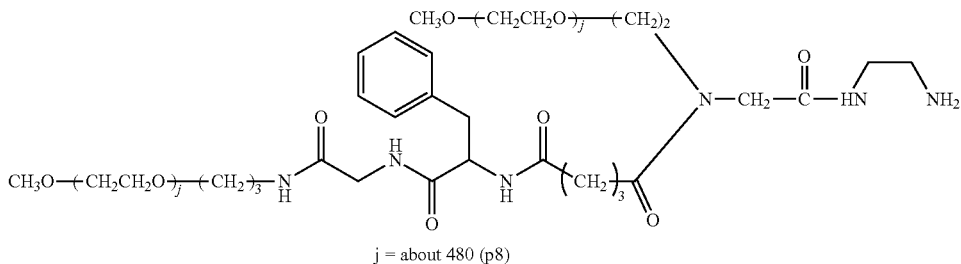

j = about 480 (p8)

The compound (p7) (2.0 g) obtained in Example 1-7 and N-Fmoc-ethylenediamine (32 mg) were dissolved in acetonitrile (5.0 g). Thereafter, diisopropylethylamine (16 mg) and DMT-MM (415 mg) were added, and the mixture was reacted at room temperature under a nitrogen atmosphere for 2 hr. Thereafter, piperidine (107 mg) was added, and the mixture was reacted at room temperature under a nitrogen atmosphere for 2 hr. After completion of the reaction, the mixture was concentrated, the concentrate was redissolved in chloroform (50 g), and the mixture was washed with 20% brine (25 g) added thereto by stirring at room temperature for 15 min, and the organic layer was recovered. To the obtained organic layer was added magnesium sulfate (10 g), and the mixture was dehydrated by stirring at room temperature for 30 min, and suction filtered using 5A filter paper. The obtained filtrate was concentrated at 40° C., the concentrate was dissolved in toluene (100 g) added thereto, hexane (50 g) was added, and the mixture was stirred at room temperature for 15 min. The resultant product was precipitated and suction filtered using 5A filter paper. The precipitate was recovered, washed with hexane (30 g) containing BHT (6 mg), suction filtered using 5A filter paper, and dried in vacuo to give the above-mentioned compound (p8). yield 1.3 g.

HPLC: The amine purity was 93%.

$^1$H-NMR (d$_6$-DMSO): 1.62 ppm (m, 2H, CO—NH—CH$_2$—<u>CH$_2$</u>—CH$_2$—O—(CH$_2$—CH$_2$—O)j-CH$_3$), 1.64 ppm (broad, <u>1H</u>), 2.05 ppm (dd, 2H, —NH—CO—CH$_2$—<u>CH$_2$</u>—CH$_2$—CO—), 2.30 ppm (m, 4H, —NH—CO—<u>CH$_2$</u>—CH$_2$—<u>CH$_2$</u>—CO—), 2.59 ppm (dd, 1H, —NH—CO—CH—<u>CH$_2$</u>—C$_6$H$_5$), 2.76 ppm (m, 2H, —NH—CH$_2$—<u>CH$_2$</u>—<u>NH$_2$</u>), 2.98 ppm (dd, 1H, —NH—CO—CH—CH$_2$—C$_6$H$_5$), 3.24 ppm (s, 3H, —NH—CH$_2$—CH$_2$—(O—CH$_2$—CH$_2$)j-O—<u>CH$_3$</u>), 3.48 ppm (m, about 3,800H, —CH$_2$—NH—CH$_2$—CH$_2$—(O—<u>CH$_2$—CH$_2$</u>)j-O—CH$_3$), 7.24 ppm (m, 6H, —NH—CO—CH—CH$_2$—<u>C$_6$H$_5$</u>, —NH—), 7.73 ppm (t, 1H), 7.80 ppm (broad, 1H), 8.12 ppm (broad, 1H)

Example 3

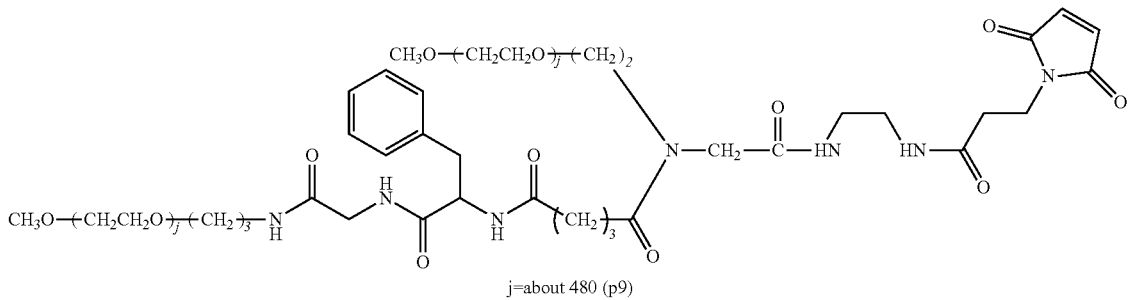

j=about 480 (p9)

The compound (p7) (300 mg) obtained in Example 1-7 was dissolved in acetonitrile (2 g). Thereafter, N-hydroxysuccinimide (6 mg) and dicyclohexylcarbodiimide (6 mg) were added, and the mixture was reacted at 40° C. under a nitrogen atmosphere for 3 hr. Thereafter, triethylamine (3 mg) and N-(2-aminoethyl)maleimide hydrochloride (5 mg) were added, and the mixture was reacted at 40° C. under a nitrogen atmosphere for 3 hr. After completion of the reaction, the mixture was concentrated, the concentrate was dissolved in ethyl acetate (50 g), hexane (30 g) was added and the mixture was stirred at room temperature for 15 min. The resultant product was precipitated and suction filtered using 5A filter paper. The precipitate was recovered, dissolved again in ethyl acetate (50 g), hexane (30 g) was added, and the mixture was stirred at room temperature for 15 min, by which the resultant product was precipitated. The precipitate was suction filtered using 5A filter paper. The precipitate was recovered, washed with hexane (30 g) containing BHT (6 mg), suction filtered using 5A filter paper, and dried in vacuo to give the above-mentioned compound (p9). yield 264 mg. The maleimide purity was 92% ($^1$H-NMR).

$^1$H-NMR ($d_6$-DMSO): 1.62 ppm (m, 2H, CO—NH—CH$_2$—<u>CH$_2$</u>—CH$_2$—O—(CH$_2$—CH$_2$—O)j-CH$_3$), 1.64 ppm (broad, 1H), 2.05 ppm (dd, 2H, —NH—CO—CH$_2$—<u>CH$_2$</u>—CH$_2$—CO—), 2.30 ppm (m, 4H, —NH—CO—<u>CH$_2$</u>—CH$_2$—<u>CH$_2$</u>—CO—), 2.59 ppm (dd, 1H, —NH—CO—CH—<u>CH$_2$</u>—C$_6$H$_5$), 2.66 ppm (t, 2H, —NH—CO—CH$_2$—CH$_2$-Maleimide), 2.98 ppm (dd, 1H, —NH—CO—CH—<u>CH$_2$</u>—C$_6$H$_5$), 3.24 ppm (s, 3H, —NH—CH$_2$—CH$_2$—(O—CH$_2$—CH$_2$)j-O—<u>CH$_3$</u>), 3.48 ppm (m, about 3,800H, —CH$_2$—NH—CH$_2$—CH$_2$—(O—<u>CH$_2$</u>—<u>CH$_2$</u>)j-O—CH$_3$), 4.76 ppm (t, 2H, —NH—CO—CH$_2$—<u>CH$_2$</u>-Maleimide), 6.98 ppm (s, 2H, —CO—<u>CH</u>—<u>CH</u>—CO—), 7.24 ppm (m, 6H, —NH—CO—CH—CH$_2$—<u>C$_6$H$_5$</u>, —NH—), 7.73 ppm (t, 1H), 7.80 ppm (broad, 1H), 8.01 ppm (broad, 1H), 8.12 ppm (broad, 1H)

Example 4

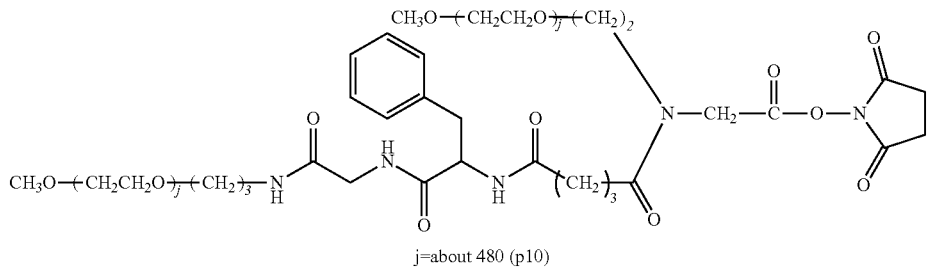

j=about 480 (p10)

The compound (p7) (1.2 g) obtained in Example 1-7 was dissolved in toluene (6 g) added thereto by heating at 40° C. Thereafter, N-hydroxysuccinimide (24 mg) and dicyclohexylcarbodiimide (24 mg) were added, and the mixture was reacted at 40° C. under a nitrogen atmosphere for 3 hr. After completion of the reaction, the mixture was suction filtered using 5A filter paper, the obtained filtrate was diluted with ethyl acetate (100 g), hexane (50 g) was added, and the mixture was stirred at room temperature for 30 min. The resultant product was precipitated and suction filtered using 5A filter paper. The precipitate was recovered, washed with hexane (50 g) containing BHT (10 mg), suction filtered using 5A filter paper, and dried in vacuo to give the above-mentioned compound (p10). yield 1.0 g. The active ester purity was 91% ($^1$H-NMR).

$^1$H-NMR ($d_6$-DMSO): 1.62 ppm (m, 2H, CO—NH—CH$_2$—<u>CH$_2$</u>—CH$_2$—O—(CH$_2$—CH$_2$—O)j-CH$_3$), 1.64 ppm (broad, 1H), 2.05 ppm (dd, 2H, —NH—CO—CH$_2$—<u>CH$_2$</u>—CH$_2$—CO—), 2.30 ppm (m, 4H, —NH—CO—<u>CH$_2$</u>—CH$_2$—<u>CH$_2$</u>—CO—), 2.59 ppm (dd, 1H, —NH—CO—CH—<u>CH$_2$</u>—C$_6$H$_5$), 2.72 ppm (s, 4H, —CO—<u>CH$_2$</u>—<u>CH$_2$</u>—CO—), 2.98 ppm (dd, 1H, —NH—CO—CH—<u>CH$_2$</u>—C$_6$H$_5$), 3.24 ppm (s, 3H, —NH—CH$_2$—CH$_2$—(O—CH$_2$—CH$_2$)j-O—<u>CH$_3$</u>), 3.48 ppm (m, about 3,800H, —CH$_2$—NH—CH$_2$—CH$_2$—(O—<u>CH$_2$</u>—<u>CH$_2$</u>)j-O—CH$_3$), 4.61 ppm (—<u>CH$_2$</u>—OCO-Succinimide), 7.24 ppm (m, 6H, —NH—CO—CH—CH$_2$—<u>C$_6$H$_5$</u>, 7.73 ppm (t, 1H), 8.12 ppm (broad, 1H)

Example 5

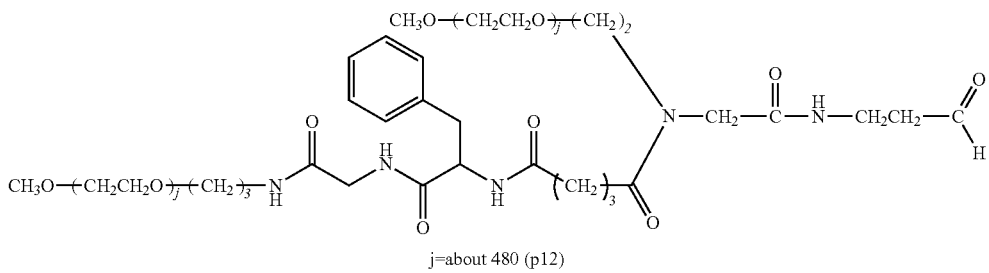

j=about 480 (p12)

Example 5-1

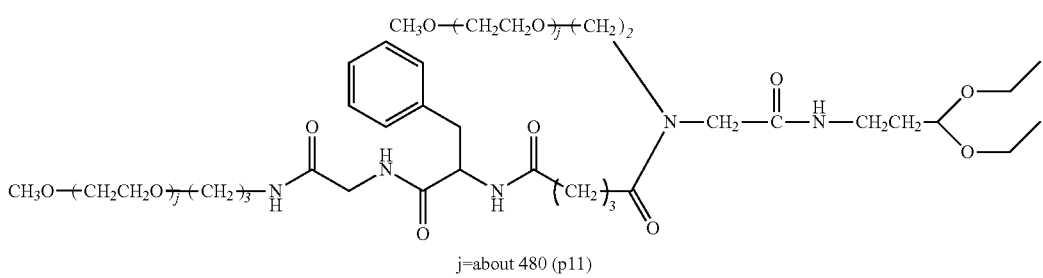

j=about 480 (p11)

The compound (p7) (800 mg) obtained in Example 1-7 was dissolved in toluene (7 g) by heating at 40° C., 3-aminopropionaldehyde diethyl acetal (9 mg) was added, and the mixture was reacted at 50° C. under a nitrogen atmosphere for 2 hr. After completion of the reaction, ethyl acetate (100 g) was added, and the mixture was stirred until uniform, hexane (50 g) was added, and the mixture was stirred at room temperature for 15 min. The resultant product was precipitated and suction filtered using 5A filter paper. The precipitate was recovered, washed with hexane (50 g) containing BHT (10 mg), suction filtered using 5A filter paper, and dried in vacuo to give the above-mentioned compound (p11). yield 684 mg.

$^1$H-NMR (d$_6$-DMSO): 1.20 ppm (t, 6H (CH$_3$—CH$_2$—O)$_2$—CH—) 1.62 ppm (m, 2H, CO—NH—CH$_2$—CH$_2$—CH$_2$—O—(CH$_2$—CH$_2$—O)j-CH$_3$), 1.64 ppm (broad, 1H), 1.85 ppm (dd, 2H, —NH—CH$_2$—CH$_2$—CH—(O—CH$_2$—CH$_3$)$_2$), 2.05 ppm (dd, 2H, —NH—CO—CH$_2$—CH$_2$—CH$_2$—CO—), 2.30 ppm (m, 4H, —NH—CO—CH$_2$—CH$_2$—CH$_2$—CO—), 2.59 ppm (dd, 1H, —NH—CO—CH—CH$_2$—C$_6$H$_5$), 2.98 ppm (dd, 1H, —NH—CO—CH—CH$_2$—C$_6$H$_5$), 3.24 ppm (s, 3H, —NH—CH$_2$—CH$_2$—(O— CH$_2$—CH$_2$)j-O—CH$_3$), 3.48 ppm (m, about 3,800H, —CH$_2$—NH—CH$_2$—CH$_2$—(O—CH$_2$—CH$_2$)j-O—CH$_3$), 3.91 ppm (—CH$_2$—CO—NH—CH$_2$—CH$_2$—CH—(O—CH$_2$—CH$_3$)$_2$), 4.55 ppm (t, 1H, —CH—(O—CH$_2$—CH$_3$)$_2$) 7.24 ppm (m, 6H, —NH—CO—CH—CH$_2$—C$_6$H$_5$, —NH—), 7.73 ppm (t, 1H), 8.12 ppm (broad, 1H)

Example 5-2

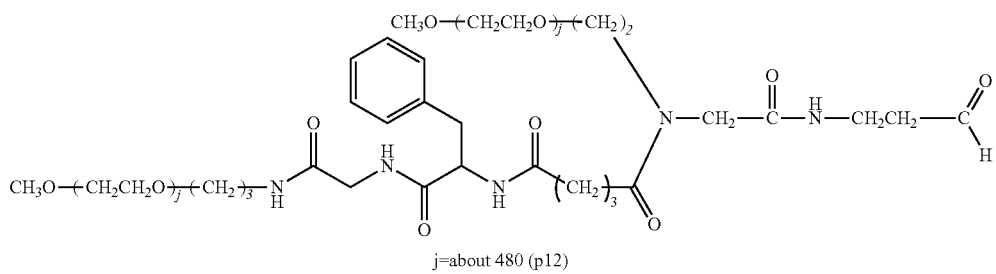

j=about 480 (p12)

The compound (p11) (600 mg) obtained in Example 5-1 was dissolved in phosphate buffer (6.0 g) adjusted to pH 1.90, and the mixture was reacted at room temperature under a nitrogen atmosphere for 3 hr. After the reaction, 0.1N aqueous sodium hydroxide solution was added to adjust to pH 6.5, and sodium chloride (1.5 g) was added and dissolved therein. To the obtained solution was added 0.1N aqueous sodium hydroxide solution to adjust the pH to 7.10, chloroform (10 g) containing BHT (2 mg) was added, and the mixture was stirred at room temperature for 20 min. The resultant product was extracted into the organic layer. The organic layer and the aqueous layer were separated, the organic layer was recovered, chloroform (20 g) containing BHT (4 mg) was added again to the aqueous layer, and the mixture was stirred at room temperature for 20 min. The resultant product was extracted into the organic layer. The organic layers obtained by the first extraction and the second extraction were combined and concentrated at 40° C., the obtained concentrate was dissolved in ethyl acetate (50 g), hexane (30 g) was added, and the mixture was stirred at room temperature for 15 min to allow for precipitation of the resultant product which was suction filtered using 5A filter paper. The precipitate was recovered, washed with hexane (30 g) containing BHT (6 mg), suction filtered using 5A filter paper, and dried in vacuo to give the above-mentioned compound (p12). yield 457 mg. The aldehyde purity was 90% ($^1$H-NMR).

$^1$H-NMR (d$_6$-DMSO): 1.62 ppm (m, 2H, CO—NH—CH$_2$—CH$_2$—CH$_2$—O—(CH$_2$—CH$_2$—O)j-CH$_3$), 1.64 ppm (broad, 1H), 2.05 ppm (dd, 2H, —NH—CO—CH$_2$—CH$_2$—CH$_2$—CO—), 2.30 ppm (m, 4H, —NH—CO—CH$_2$—CH$_2$—CH$_2$—CO—), 2.59 ppm (dd, 1H, —NH—CO—CH—CH$_2$—C$_6$H$_5$), 2.66 ppm (dd, 2H, —CO—NH—CH$_2$—CH$_2$—CHO), 2.98 ppm (dd, 1H, —NH—CO—CH—CH$_2$—C$_6$H$_5$), 3.24 ppm (s, 3H, —NH—CH$_2$—CH$_2$—(O—CH$_2$—CH$_2$)j-O—CH$_3$), 3.48 ppm (m, about 3,800H, —CH$_2$—NH—CH$_2$—CH$_2$—(O—CH$_2$—CH$_2$)j-O—CH$_3$), 3.91 ppm (s, 2H, —CH$_2$—CO—NH—CH$_2$—CH$_2$—CHO) 7.24 ppm (m, 6H, —NH—CO—CH—CH$_2$—C$_6$H$_5$, —NH—), 7.73 ppm (t, 1H), 8.12 ppm (broad, 1H), 9.72 ppm (s, 1H, —CO—NH—CH$_2$—CH$_2$—CHO)

Example 6

Example 6-1

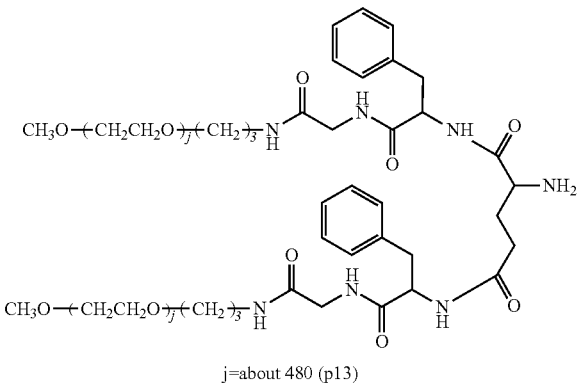

j=about 480 (p13)

L-glutamic acid with the N-terminal protected by a 9-fluorenylmethyloxycarbonyl group (Fmoc group) (Fmoc-Glu-OH) (16.0 mg) and the compound (p4) (2.0 g) obtained in Example 1-4 were dissolved in acetonitrile (10 g) added thereto by heating at 30° C. Thereafter, diisopropylethylamine (15 mg) and DMT-MM (39.0 mg) were added, and the mixture was reacted at room temperature under a nitrogen atmosphere for 1 hr. Thereafter, piperidine (111 mg) was added, and the mixture was reacted at room temperature under a nitrogen atmosphere for 2 hr. After completion of the reaction, the reaction mixture was diluted with toluene (80 g), hexane (40 g) was added, and the mixture was stirred at room temperature for 15 min. The resultant product was precipitated and suction filtered using 5A filter paper. The precipitate was recovered, dissolved again in toluene (100 g), hexane (50 g) was added, and the mixture was stirred at room temperature for 15 min. The resultant product was precipitated and suction filtered using 5A filter paper. The precipitate was recovered, washed with hexane (50 g) containing BHT (10 mg), suction filtered using 5A filter paper, and dried in vacuo to give the above-mentioned compound (p13). yield 1.6 g.

HPLC: amine purity 92%.

$^1$H-NMR (d$_6$-DMSO): 1.54 ppm (m, 2H, —NH—CO—CH(NH$_2$)—CH$_2$—CH$_2$—), 1.62 ppm (m, 4H, —CO—

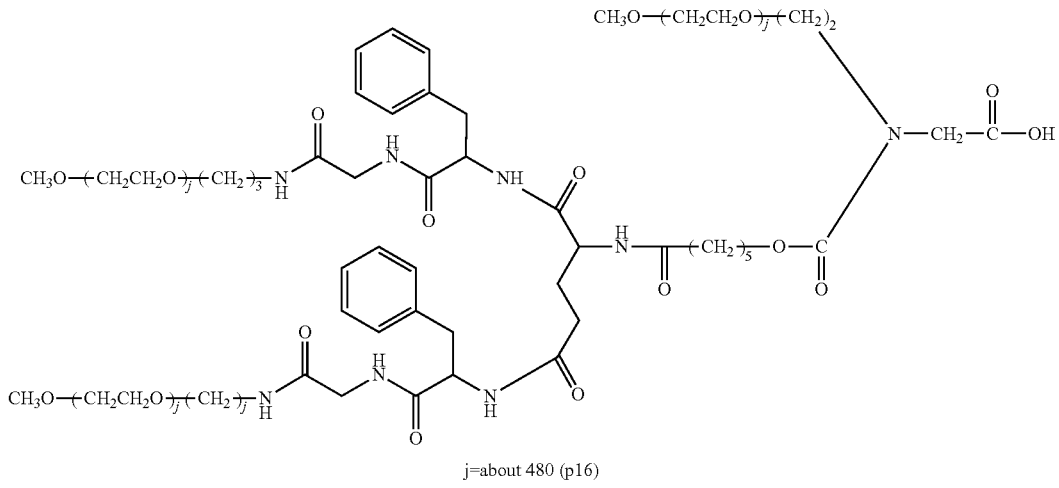

j=about 480 (p16)

NH—CH$_2$—CH$_2$—CH$_2$—), 1.97 ppm (m, 2H, —NH—CO—CH(NH$_2$)—CH$_2$—CH$_2$—), 2.74 ppm (dd, 1H, —CO—NH—CH—CH$_2$—C$_6$H$_5$), 2.81 ppm (dd, 1H, —CO—NH—CH—CH$_2$—C$_6$H$_5$), 3.11 ppm (m, 11H), 3.24 ppm (s, 6H, —CO—NH—CH$_2$—CH$_2$—CH$_2$—O—(CH$_2$—CH$_2$—O)j-CH$_3$), 3.64 ppm (m, about 3,800H, —CO—NH—CH$_2$—CH$_2$—CH$_2$—O—(CH$_2$—CH$_2$—O)j-CH$_3$), 4.49 ppm (m, 1H, —CO—NH—CH—CH$_2$—C$_6$H$_5$), 4.57 ppm (m, 1H, —CO—NH—CH—CH$_2$—C$_6$H$_5$), 7.25 ppm (m, 10H, —CO—NH—CH—CH$_2$—C$_6$H$_5$), 7.74 ppm (m, 2H), 8.44 ppm (m, 2H), 8.61 ppm (m, 2H)

Example 6-2

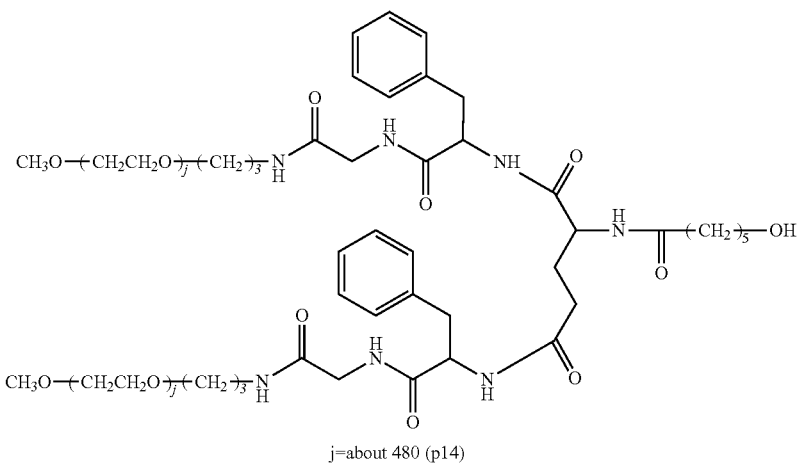

j=about 480 (p14)

ε-caprolactone (114 mg) was dissolved in 1N NaOH (0.8 mL) and reacted for 2 hr to prepare a 6-hydroxycaproic acid aqueous solution (0.88 M). The compound (p13) (1.5 g) obtained in Example 6-1 was dissolved in acetonitrile (6 g). Thereafter, the above-mentioned 6-hydroxycaproic acid aqueous solution (80 μL), diisopropylethylamine (15 mg), and DMT-MM (16 mg) were added, and the mixture was reacted at room temperature under a nitrogen atmosphere for 1 hr. After completion of the reaction, the reaction mixture was concentrated at 40° C., and the obtained concentrate was dissolved in chloroform (30 g) added thereto. A saturated aqueous sodium hydrogen carbonate solution (15 g) was added, and the mixture was washed by stirring at room temperature for 15 min. The aqueous layer and the organic layer were separated, to the organic layer was added again a saturated aqueous sodium hydrogen carbonate solution (15 g), and the mixture was washed by stirring at room temperature for 15 min, and the organic layer was recovered. To the obtained chloroform solution was added magnesium sulfate (5 g), and the mixture was dehydrated by stirring for 30 min and suction filtered using 5A filter paper. The obtained filtrate was concentrated at 40° C., to the concentrate was added ethyl acetate (50 g), and the mixture was stirred until uniform. Hexane (25g) was added, and the mixture was stirred at room temperature for 15 min. The resultant product was precipitated and suction filtered using 5A filter paper. The precipitate was recovered, dissolved again in ethyl acetate (50 g), hexane (25 g) was added, and the mixture was stirred at room temperature for 15 min. The resultant product was precipitated and suction filtered using 5A filter paper. The precipitate was recovered, washed with hexane (50 g) containing BHT (10 mg), suction filtered using 5A filter paper, and dried in vacuo to give the above-mentioned compound (p14). yield 1.2 g.

$^1$H-NMR (CDCl$_3$): 1.37 ppm (m, 2H, HO—CH$_2$—CH$_2$—CH$_2$—CH$_2$—CH$_2$—CO—NH—), 1.55 ppm (m, 4H, HO—CH$_2$—CH$_2$—CH$_2$—CH$_2$—CH$_2$—CO—NH—), 1.77 ppm (m, 4H, —CO—NH—CH$_2$—CH$_2$—CH$_2$—O—(CH$_2$—CH$_2$—O)j-CH$_3$), 1.85 ppm (m, 1H), 2.01 ppm (m, 2H, HO—CH$_2$—CH$_2$—CH$_2$—CH$_2$—CH$_2$—CO—NH—), 3.01 ppm (m, 1H), 3.24 ppm (m, 8H), 3.38 ppm (s, 6H, —CO—NH—CH$_2$—CH$_2$—CH$_2$—O—(CH$_2$—CH$_2$—O)j-CH$_3$), 3.64 ppm (m, about 3,800H, —CO—NH—CH$_2$—CH$_2$—CH$_2$—O—(CH$_2$—CH$_2$—O)j-CH$_3$), 4.03 ppm (m, 4H), 4.14 ppm (m, 1H), 4.48 ppm (m, 2H, —CO—NH—CH—CH$_2$—C$_6$H$_5$), 6.95 ppm (broad, 1H), 7.00 ppm (broad, 1H), 7.26 ppm (m, 10H, —CO—NH—CH—CH$_2$—C$_6$H$_5$), 7.66 ppm (broad, 1H), 8.29 ppm (broad, 1H)

Example 6-3

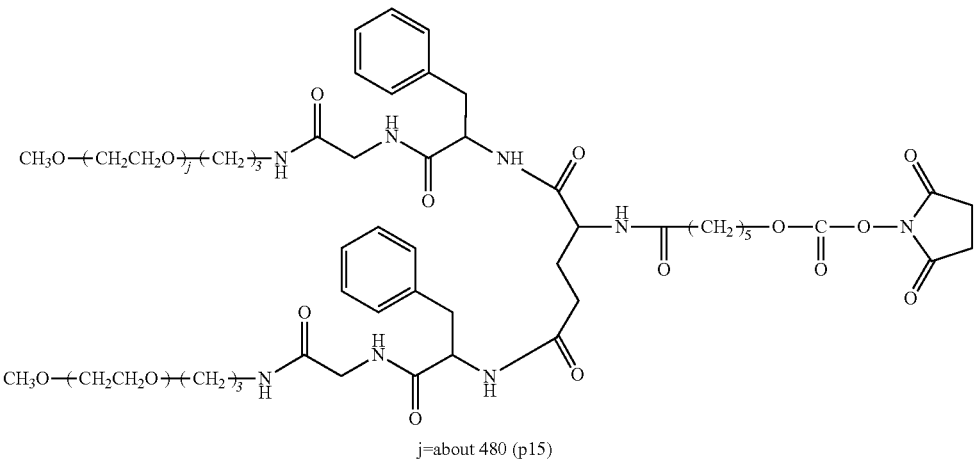

j=about 480 (p15)

The compound (p14) (500 mg) obtained in Example 6-2 was dissolved in dichloromethane (3.5 g). Thereafter, di(N-succinimidyl) carbonate (51 mg) and pyridine (20 mg) were added, and the mixture was reacted at room temperature under a nitrogen atmosphere for 8 hr. After completion of the reaction, the reaction mixture was washed with 5% brine (5 g), magnesium sulfate (0.1 g) was added, and the mixture was stirred at 25° C. for 30 min and suction filtered using 5A filter paper. The obtained filtrate was concentrated, the concentrate was dissolved in ethyl acetate (100 g) added thereto, hexane (50 g) was added, and the mixture was stirred at room temperature for 15 min. The resultant product was precipitated and suction filtered using 5A filter paper. The precipitate was recovered, washed with hexane (25 g) containing BHT (5 mg), suction filtered using 5A filter paper, and dried in vacuo to give the above-mentioned compound (p15). yield 286 mg. The active carbonate purity was 91% ($^1$H-NMR)

$^1$H-NMR (CDCl$_3$): 1.38 ppm (m, 2H, Succinimide-OCO—CH$_2$—CH$_2$—CH$_2$—CH$_2$—CH$_2$—CO—NH—), 1.59 ppm (m, 2H, Succinimide-OCO—CH$_2$—CH$_2$—CH$_2$—CH$_2$—CH$_2$—CO—NH—), 1.75 ppm (m, 6H), 1.85 ppm (m, 1H), 2.13 ppm (m, 2H, Succinimide-OCO—CH$_2$—CH$_2$—CH$_2$—CH$_2$—CH$_2$—CO—NH—), 2.83 ppm (s, 4H, —CO—CH$_2$—CH$_2$—CO—), 3.01 ppm (m, 1H), 3.19 ppm (m, 6H), 3.38 ppm (s, 6H, —CO—NH—CH$_2$—CH$_2$—CH$_2$—O—(CH$_2$—CH$_2$—O)j-CH$_3$), 3.64 ppm (m, about 3,800H, —CO—NH—CH$_2$—CH$_2$—CH$_2$—O—(CH$_2$—CH$_2$—O)j-CH$_3$), 4.03 ppm (m, 3H), 4.18 ppm (m, 1H), 4.31 ppm (t, 2H, Succinimide-OCO—CH$_2$—CH$_2$—CH$_2$—CH$_2$—CH$_2$—CO—NH—), 4.50 ppm (m, 2H, —CO—NH—CH—CH$_2$—C$_6$H$_5$), 6.98 ppm (broad, 1H), 7.15 ppm (broad, 1H), 7.26 ppm (m, 10H, —CO—NH—CH—CH$_2$—C$_6$H$_5$), 7.81 ppm (broad, 1H), 8.37 ppm (broad, 1H)

Example 6-4

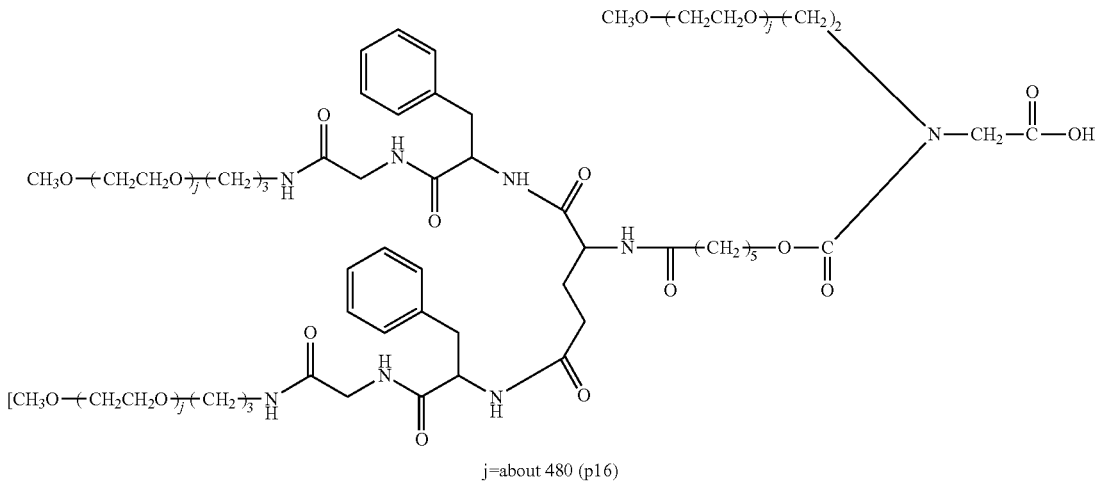

j=about 480 (p16)

The compound (p2) (125 mg) obtained in Example 1-2 and the compound (p15) (250 mg) obtained in Example 6-3 were dissolved in dichloromethane (50 g), triethylamine (0.5 g) was added, and the mixture was reacted at room temperature for 8 hr. After the reaction, the reaction mixture was washed with 20% brine (20 g) added thereto by stirring at room temperature for 15 min, and the organic layer was recovered. To the organic layer was added magnesium sulfate (5 g), and the mixture was stirred at room temperature for 15 min and suction filtered using 5A filter paper. The obtained filtrate was concentrated, the concentrate was dissolved in ethyl acetate (100 g), hexane (50 g) was added, and the mixture was stirred at room temperature for 15 min. The resultant product was precipitated and suction filtered using 5A filter paper. The precipitate was recovered, washed with hexane (20 g) containing BHT (4 mg), suction filtered using 5A filter paper, and dried in vacuo to give the above-mentioned compound (p16). yield 242 mg.

HPLC: The carboxylic acid purity was 90%

$^1$H-NMR (d$_6$-DMSO): 1.29 ppm (m, 2H, —NH—CO—CH$_2$—CH$_2$—CH$_2$—CH$_2$—CH$_2$—OCO—), 1.58 ppm (m, 4H, —NH—CO—CH$_2$—CH$_2$—CH$_2$—CH$_2$—CH$_2$—OCO—), 1.75 ppm (m, 6H), 1.85 ppm (m, 1H), 2.13 ppm (m, 2H, —NH—CO—CH$_2$—CH$_2$—CH$_2$—CH$_2$—CH$_2$—OCO—), 3.01 ppm (m, 1H), 3.19 ppm (m, 6H), 3.38 ppm (s, 6H, —CO—NH—CH$_2$—CH$_2$—CH$_2$—O—(CH$_2$—CH$_2$—O)j-CH$_3$), 3.64 ppm (m, about 5,700H, —CO—NH—CH$_2$—CH$_2$—CH$_2$—O—(CH$_2$—CH$_2$—O)j-CH$_3$), 3.90 ppm (t, 2H, —NH—CO—CH$_2$—CH$_2$—CH$_2$—CH$_2$—CH$_2$—OCO—) 4.03 ppm (m, 3H), 4.18 ppm (m, 1H), 4.37 ppm (s, 2H, —CH$_2$—COOH)4.50 ppm (m, 2H, —CO—NH—CH—CH$_2$—C$_6$H$_5$), 6.98 ppm (broad, 1H), 7.15 ppm (broad, 1H), 7.26 ppm (m, 10H, —CO—NH—CH—CH$_2$—C$_6$H$_5$), 7.81 ppm (broad, 1H), 8.37 ppm (broad, 1H)

Comparative Example 1

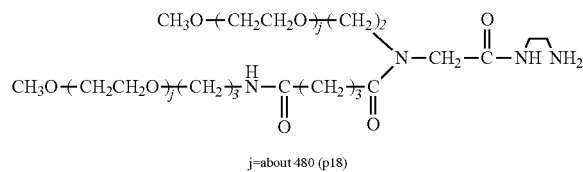

j=about 480 (p18)

Comparative Example 1-1

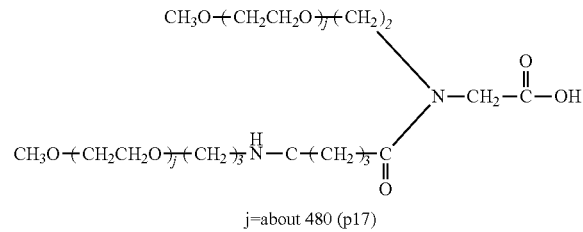

j=about 480 (p17)

The compound (1 g) obtained in Example 1-2 and "SUNBRIGHT ME-200GS3" (1 g) having an average molecular weight of 20,000, manufactured by NOF CORPORATION, were dissolved in dichloromethane (20 g), triethylamine (0.2 g) was added, and the mixture was reacted at room temperature for 8 hr. After the reaction, the reaction mixture was washed with 20% brine (10 g) added thereto by stirring at room temperature for 15 min, and the organic layer was recovered. To the organic layer was added magnesium sulfate (3 g), and the mixture was stirred at room temperature for 15 min and suction filtered using 5A filter paper. The obtained filtrate was concentrated, the concentrate was dissolved in ethyl acetate (100 g), hexane (50 g) was added, and the mixture was stirred at room temperature for 15 min. The resultant product was precipitated and suction filtered using 5A filter paper. The precipitate was recovered, washed with hexane (30 g) containing BHT (6 mg), suction filtered using 5A filter paper, and dried in vacuo to give the above-mentioned compound (p17). yield 1.2 g.

HPLC: The carboxylic acid purity was 93%.

$^1$H-NMR (d$_6$-DMSO): 1.73 ppm (m, 2H, —CO—NH—CH$_2$—CH$_2$—CH$_2$—(O—CH$_2$—CH$_2$)j-), 2.03 ppm (m, 2H, —NH—CO—CH$_2$—CH$_2$—CH$_2$—CO—N—), 2.34 ppm (t, 4H, —NH—CO—CH$_2$—CH$_2$—CH$_2$—CO—N—), 3.40 ppm (s, 6H, —(O—CH$_2$—CH$_2$)j-O—CH$_3$), 3.55 ppm (m, about 3,800H, —CH$_2$—(O—CH$_2$—CH$_2$)j-O—CH$_3$), 4.61 ppm (s, 2H, —CH$_2$—COOH), 7.70 ppm (broad, 1H, —CH$_2$—NH—CO—CH$_2$—CH$_2$—CH$_2$—CO—)

Comparative Example 1-2

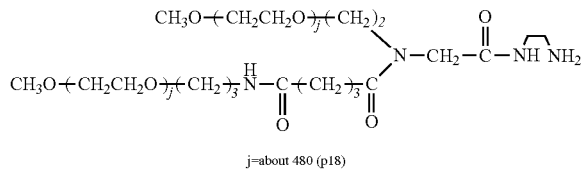

j=about 480 (p18)

The compound (p17) (1.0 g) obtained in Comparative Example 1-1 and N-Fmoc-ethylenediamine (16 mg) were dissolved in acetonitrile (2.5 g). Thereafter, diisopropylethylamine (8 mg) and DMT-MM (208 mg) were added, and the mixture was reacted at room temperature under a nitrogen atmosphere for 2 hr. Thereafter, piperidine (107 mg) was added, and the mixture was reacted at room temperature under a nitrogen atmosphere for 2 hr. After completion of the reaction, the reaction mixture was concentrated, and the concentrate was redissolved in chloroform (50 g), washed with 20% brine (25 g) added thereto by stirring at room temperature for 15 min, and the organic layer was recovered. To the obtained organic layer was added magnesium sulfate (10 g), and the mixture was dehydrated by stirring at room temperature for 30 min and suction filtered using 5A filter paper. The obtained filtrate was concentrated at 40° C., the concentrate was dissolved in toluene (100 g) added thereto, hexane (50 g) was added, and the mixture was stirred at room temperature for 15 min. The resultant product was precipitated and suction filtered using 5A filter paper. The precipitate was recovered, washed with hexane (30 g) containing BHT (6 mg), suction filtered using 5A filter paper, and dried in vacuo to give the above-mentioned compound (p8). yield 581 mg.

HPLC: The amine purity was 90%.

$^1$H-NMR (d$_6$-DMSO): 1.73 ppm (m, 2H, —CO—NH—CH$_2$—CH$_2$—CH$_2$—(O—CH$_2$—CH$_2$)j-), 2.03 ppm (m, 2H, —NH—CO—CH$_2$—CH$_2$—CH$_2$—CO—N—), 2.34 ppm (t, 4H, —NH—CO—CH$_2$—CH$_2$—CH$_2$—CO—N—), 2.76 ppm (m, 2H, —CH$_2$—CO—NH—CH$_2$—CH$_2$—NH$_2$), 3.40 ppm (s, 6H, —(O—CH$_2$—CH$_2$)j-O—CH$_3$), 3.55 ppm (m, about 3,800H, —CH$_2$—(O—CH$_2$—CH$_2$)j-O—CH$_3$) 3.66 ppm (m, 2H, —CH$_2$—CO—NH—CH$_2$—CH$_2$—NH$_2$), 3.91 ppm (s, 2H, —N—CH$_2$—CO—NH—), 7.70 ppm (broad, 1H, —CH$_2$—NH—CO—CH$_2$—CH$_2$—CH$_2$—CO—), 7.83 ppm (broad, 1H, —CH$_2$—CO—NH—CH$_2$—CH$_2$—NH$_2$)

Example 8

Stability Test in Serum

Mouse or human serum (1 mL) was added to a 1.5 mL Eppendorf tube, and compound (p8) which is a branched degradable polyethylene glycol derivative obtained in Example 2, compound (p18) which is a non-degradable polyethylene glycol derivative obtained in Comparative Example 1-2, and methoxy PEG amine 40 kDa were respectively added to a concentration of 5.0 mg/mL. After incubation at 37° C. for 96 hr, 200 μL was sampled. Acetonitrile was added thereto, and the mixture was stirred by vortex for 1 min to precipitate the protein in serum. After centrifugation, the supernatant was collected. Then, to remove hydrophobic substances such as fatty acid and the like, hexane was added to the collected liquid, and the mixture was stirred by vortex for 1 min, centrifuged, and the lower layer was collected. This solution was concentrated under vacuum conditions and the polyethylene glycol derivative was recovered from the serum. Then, GPC analysis was performed and the degradation rate of the degradable polyethylene glycol derivative was calculated.

The degradation rate was calculated by the following formula.

degradation rate=(peak area % at 40 kDa before test−peak area % at 40 kDa after test)÷(peak area % at 40 kDa before test)×100

The results are shown in Table 1.

TABLE 1

| sample name | | degradation rate in mouse serum | degradation rate in human serum |
|---|---|---|---|
| Example 2 | compound (p8) | 1% | 1% |
| Comparative Example 1 | compound (p18) | 0% | 1% |
| non-degradable | methoxy PEG amine 40kDa | 0% | 0% |

According to Table 1, the compound (p8), which is a branched degradable polyethylene glycol derivative, was not degraded in the serum, similar to compound (p18) which is a non-degradable polyethylene glycol derivative and methoxy PEG amine 40 kDa. That is, it was shown that the degradable polyethylene glycol derivative is stable in blood.

Example 9

Degradability Test Using Cells

Using medium RPMI-1640 (10% FBS Pn/St) (10 mL), RAW264.7 was seeded at $10 \times 10^6$ cells in a 100 mm dish, and cultured at 37° C. for 24 hr. The medium was each exchanged with a medium in which compound (p8) which is a branched degradable polyethylene glycol derivative obtained in Example 2, compound (p18) which is a non-degradable polyethylene glycol derivative obtained in Comparative Example 1-2, and methoxy PEG amine 40 kDa had been dissolved at a concentration of 10 mg/mL, and the cells were cultured at 37° C. for 96 hr. After culturing, the cells were lysed with 1% SDS solution, diluted with PBS, acetonitrile was added thereto, and the mixture was stirred for 1 min by vortex to precipitate the protein in the cell lysate, and after centrifugation, the supernatant was collected. Then, to remove hydrophobic substances such as fatty acids, hexane was added to the recovered liquid, and the mixture was stirred by vortex for 1 min, centrifuged, and the lower layer was recovered. This solution was concentrated under vacuum conditions to recover the polyethylene glycol derivative from the cells.

To confirm the degradation in the medium used for cell culture, media in which various polyethylene glycol derivatives had been dissolved at a concentration of 10 mg/mL were only cultured at 37° C. for 96 hr, and the polyethylene glycol derivative was recovered by the same operation as that described above.

Thereafter, the collected various polyethylene glycol derivatives were subjected to GPC analysis, and the degradation rate of the branched degradable polyethylene glycol derivative was calculated by the same calculation formula as in Example 8.

The results are shown in Table 2.

TABLE 2

| sample name | | degradation rate in medium | degradation rate in cell |
|---|---|---|---|
| Example 2 | compound (p8) | 0% | 99% |
| Comparative Example 1 | compound (p18) | 0% | 0% |
| non-degradable | methoxy PEG amine 40kDa | 0% | 0% |

According to Table 2, it could be confirmed that compound (p8) which is a branched degradable polyethylene glycol derivative is effectively degraded in the cells (degradation rate 99%), and degraded into a molecular weight of 40,000 to 20,000. The branched degradable polyethylene glycol derivative is not degraded in the medium used for cell culture. Thus, it was confirmed that it was specifically degraded in the cells. On the other hand, compound (p18) and methoxy PEG amine 40 kDa which are non-degradable polyethylene glycol derivatives were not degraded in the cells.

INDUSTRIAL APPLICABILITY

The branched degradable polyethylene glycol derivative of the present invention is a high-molecular-weight polyethylene glycol derivative that does not cause vacuolation of cells, can be effectively used for modifying bio-related substances, is stable in the blood of living organisms, and is degraded in cells.

This application is based on patent application No. 2019-176251 filed in Japan, the contents of which are encompassed in full herein.

The invention claimed is:

1. A branched degradable polyethylene glycol derivative represented by the following formula (1), comprising, in a molecule, an oligopeptide that is degraded in the cells:

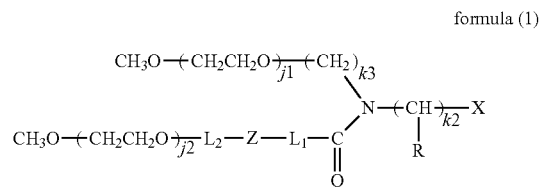

formula (1)

wherein $k_1$ and $k_2$ are each independently 1-12, $j_1$ and $j_2$ are each independently 45-950, R is a hydrogen atom, a substituted or unsubstituted alkyl group having 1-12 carbon atoms, a substituted aryl group, an aralkyl group or a heteroalkyl group, Z is an oligopeptide that is degraded by enzyme in the cells, X is a functional group capable of reacting with a bio-related substance, and $L_1$ and $L_2$ are each independently a single bond or a divalent spacer.

2. The branched degradable polyethylene glycol derivative according to claim 1, wherein the oligopeptide for Z is a degradable oligopeptide of 2-8 residues consisting of neutral amino acids excluding cysteine.

3. The branched degradable polyethylene glycol derivative according to claim 1, wherein the oligopeptide for Z is a peptide having glycine for a C-terminal amino acid.

4. The branched degradable polyethylene glycol derivative according to claim 1, wherein the oligopeptide for Z is an oligopeptide having at least one hydrophobic neutral amino acid having a hydropathy index of not less than 2.5.

5. The branched degradable polyethylene glycol derivative according to claim 1, wherein $L_1$ and $L_2$ are each independently a single bond, a urethane bond, an amide bond, an ether bond, a thioether bond, a secondary amino group, a urea bond, or an alkylene group containing such bond and/or group.

6. The branched degradable polyethylene glycol derivative according to claim 1, wherein X is selected from the group consisting of an active ester group, an active carbonate group, an aldehyde group, an isocyanate group, an isothiocyanate group, an epoxy group, a maleimide group, a vinylsulfonyl group, an acrylic group, a sulfonyloxy group, a carboxyl group, a thiol group, a dithiopyridyl group, an α-haloacetyl group, an alkynyl group, an allyl group, a vinyl group, an amino group, an oxyamino group, a hydrazide group, and an azide group.

7. A branched degradable polyethylene glycol derivative represented by the following formula (2):

formula (2)

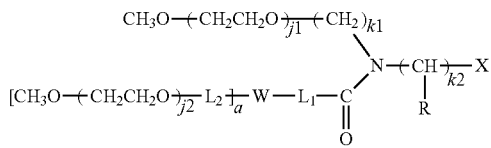

wherein $k_1$ and $k_2$ are each independently 1-12, $j_1$ and $j_2$ are each independently 45-950, R is a hydrogen atom, a substituted or unsubstituted alkyl group having 1-4 carbon atoms, a substituted aryl group, an aralkyl group or a heteroalkyl group, W is oligopeptide of 5-47 residues having a symmetrical structure centered on glutamic acid or lysine, a is 2-8, X is a functional group capable of reacting with a bio-related substance, and $L_1$ and $L_2$ are each independently a single bond or a divalent spacer.

8. The branched degradable polyethylene glycol derivative according to claim 7, wherein the oligopeptide having a symmetrical structure centered on glutamic acid or lysine for W is an oligopeptide having a structure of the following w1 or w2:

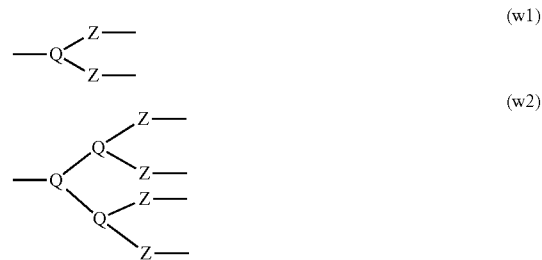

wherein Q is a residue of glutamic acid or lysine, and Z is a degradable oligopeptide of 2-5 residues consisting of neutral amino acids excluding cysteine.

9. The branched degradable polyethylene glycol derivative according to claim 8, wherein the degradable oligopeptide for Z is an oligopeptide having glycine as a C-terminal amino acid.

10. The branched degradable polyethylene glycol derivative according to claim 8, wherein the degradable oligopeptide for Z is an oligopeptide having at least one hydrophobic neutral amino acid having a hydropathy index of not less than 2.5.

11. The branched degradable polyethylene glycol derivative according to claim 7, wherein $L_1$ and $L_2$ are each independently a single bond, a urethane bond, an amide bond, an ether bond, a thioether bond, a secondary amino group, a urea bond, or an alkylene group optionally containing such bond and/or group.

12. The branched degradable polyethylene glycol derivative according to claim 7, wherein X is selected from the group consisting of an active ester group, an active carbonate group, an aldehyde group, an isocyanate group, an isothiocyanate group, an epoxy group, a maleimide group, a vinylsulfonyl group, an acrylic group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

* * * * *